(12) United States Patent
Sekiyama

(10) Patent No.: US 7,887,802 B2
(45) Date of Patent: Feb. 15, 2011

(54) IL-18 RECEPTOR ANTAGONIST AND PHARMACEUTICAL COMPOSITION CONTAINING THE ANTAGONIST

(76) Inventor: Atsuo Sekiyama, 32-1, Esaka-cho 4-chome, Suita-shi, Osaka (JP) 564-0063

( * ) Notice: Subject to any disclaimer, the term of this patent is extended or adjusted under 35 U.S.C. 154(b) by 695 days.

(21) Appl. No.: 11/632,469

(22) PCT Filed: Jul. 15, 2005

(86) PCT No.: PCT/JP2005/013167

§ 371 (c)(1),
(2), (4) Date: May 22, 2007

(87) PCT Pub. No.: WO2006/009114

PCT Pub. Date: Jan. 26, 2006

(65) Prior Publication Data

US 2008/0063644 A1 Mar. 13, 2008

(30) Foreign Application Priority Data

Jul. 16, 2004 (JP) ............................. 2004-210700

(51) Int. Cl.
*A61K 39/395* (2006.01)
*C07K 16/28* (2006.01)

(52) U.S. Cl. .............. 424/139.1; 424/143.1; 530/387.9; 530/388.1; 530/388.15; 530/389.1; 514/12

(58) Field of Classification Search ........................ None
See application file for complete search history.

(56) References Cited

U.S. PATENT DOCUMENTS

| | | | |
|---|---|---|---|
| 6,054,487 | A | 4/2000 | Sekut et al. |
| 6,600,022 | B1 | 7/2003 | Torigoe et al. |
| 2002/0098185 | A1 | 7/2002 | Sims |
| 2003/0190318 | A1 | 10/2003 | Torigoe et al. |
| 2006/0241036 | A1 | 10/2006 | Hoshino |

FOREIGN PATENT DOCUMENTS

| | | |
|---|---|---|
| EP | 1 433 484 | 4/2007 |
| JP | 11-100400 | 4/1999 |
| JP | 2002-504091 | 2/2002 |
| WO | 97/31010 | 8/1997 |
| WO | 01/62285 | 8/2001 |
| WO | 02/32374 | 4/2002 |
| WO | 2005/012352 | 2/2005 |

OTHER PUBLICATIONS

Naik et al, Journal of Investigative Dermatology, 1999, vol. 113, pp. 766-772.*
H. Rothe et al., "IL-18 Inhibits Diabetes Development in Nonobese Diabetic Mice by Counterregulation of TH-1-Dependent Destructive Insulitis[1]", The Journal of Immunology, vol. 163, pp. 1230-1236, 1999.
A. Nakata et al., "Inhibition by Interleukin 18 of Osteolytic Bone Metastasis by Human Breast Cancer Cells", Anticancer Research, vol. 19, pp. 4131-4138, 1999.
Y. Gu et al., "Activation of Interferon-γ Inducing Factor Mediated by Interleukin-1β Converting Enzyme", Science, vol. 275, pp. 206-209, Jan. 10, 1997.
K. Nakanishi et al., "Interleukin-18 Regulates Both TH1 and TH2 Responses", Annu. Rev. Immunol., vol. 19, pp. 423-474, 2001.
H. Okamura et al., "Interleukin-18 (IL-1F4)", The Cytokine Handbook Fourth Edition (Acedemic Press), vol. 2, pp. 709-733, 2002.
K. Torigoe et al., "Purification and Characterization of the Human Interleukin-18 Receptor", The Journal of Biological Chemistry, vol. 272, No. 41, pp. 25737-25742, Oct. 10, 1997.
T. K. Means et al., "Structure and Function of Toll-Like Receptor Proteins", Life Sciences, vol. 68, pp. 241-258, 2000.
Y. Wang et al., "Heat Shock Response Inhibits IL-18 Expression Through the JNK Pathway in Murine Peritoneal Macrophages", Biochemical and Biophysical Research Communications, vol. 296, pp. 742-748, 2002.
A. Arici et al., "Altered Expression of Interleukin-18 in the Peritoneal Fluid of Women with Endometriosis", Fertility and Sterility, vol. 80, No. 4, pp. 889-894, Oct. 2003.
G. Wildbaum et al., "Neutralizing Antibodies to IFN-γ-Inducing Factor Prevent Experimental Autoimmune Encephalomyelitis[1]", The Journal of Immunology, vol. 161, pp. 6368-6374, 1998.
J. M. Dayer, "Interleukin-18, Rheumatoid Arthritis, and Tissue Destruction", The Journal of Clinical Investigation, vol. 104, No. 10, pp. 1337-1339, Nov. 1999.
P. Reddy et al., "Interleukin-18 Regulates Acute Graft-Versus-Host Disease by Enhancing Fas-Mediated Donor T Cell Apoptosis", J. Exp. Med., vol. 194, No. 10, pp. 1433-1440, Nov. 19, 2001.
T. Kunikata et al., "Constitutive and Induced IL-18 Receptor Expression by Various Peripheral Blood Cell Subsets as Determined by Anti-hIL-18R Monoclonal Antibody", Cellular Immunology, vol. 189, pp. 135-143, 1998.

(Continued)

*Primary Examiner*—Bridget E Bunner
*Assistant Examiner*—Fozia M Hamud
(74) *Attorney, Agent, or Firm*—Wenderoth, Lind & Ponack, L.L.P.

(57) ABSTRACT

Provided is an IL-18 receptor antibody usable for immunohistochemistry, which functions as an IL-18 receptor antagonist. Also provided is a pharmaceutical composition and method for preventing and/or treating an IL-18-dependent disorder, particularly skin thickening caused by ultraviolet, using the antibody. An antibody against the IL-18 receptor α subunit, which is characterized by binding specifically to a polypeptide consisting of the amino acid sequence shown by SEQ ID NO:1, or an antibody against the IL-18 receptor β subunit, which is characterized by binding specifically to a polypeptide consisting of the amino acid sequence shown by SEQ ID NO:2, is prepared.

1 Claim, 13 Drawing Sheets

OTHER PUBLICATIONS

B. Zhang et al., "Expression of IL-18 and its Receptor in Human Leukemia Cells", Leukemia Research, vol. 27, pp. 813-822, 2003.

J. K. Brieland et al.,"Cytokine Networking in Lungs of Immunocompetent Mice in Response to Inhaled *Aspergillus Fumigatus*", Infection and Immunity, vol. 69, No. 3, pp. 1554-1560, Mar. 2001.

D. Xu et al., "Selective Expression and Functions of Interleukin 18 Receptor on T Helper (Th) Type 1 but not Th2 Cells", J. Exp. Med., vol. 188, No. 8, pp. 1485-1492, Oct. 19, 1998.

T. W. Lovenberg et al., "Cloning of a cDNA Encoding a Novel Interleukin-1-Receptor Related Protein (IL1R-rp2)", Journal of Neuroimmunology, vol. 70, pp. 113-122, 1996.

P. Parnet et al., "IL-1Rrp is a Novel Receptor-Like Molecule Similar to the Type I Interleukin-1 Receptor and its Homologues T1/ST2 and IL-1R AcP", The Journal of Biological Chemistry, vol. 271, No. 8, pp. 3967-3970, Feb. 23, 1996.

T. L. Born et al., "Cloning of a Novel Receptor Subunit, AcPL, Required for Interleukin-18 Signaling", The Journal of Biological Chemistry, vol. 273, No. 45, pp. 29445-29450, Nov. 6, 1998.

J. K. Lee et al., Differences in Signaling Pathways by IL-1$\beta$ and IL-18, PNAS, vol. 101, No. 23, pp. 8815-8820, Jun. 8, 2004.

J. K. Lee et al., "Differences in Signaling Pathways by IL-1$\beta$ and IL-18", Proc. Natl. Acad. Sci., vol. 101, No. 23, pp. 8815-8820, Jun. 8, 2004.

Supplementary European Search Report issued Mar. 16, 2009 in European Application No. 05 76 6266.

R. Debets et al., "IL-18 Receptors, Their Role in Ligand Binding and Function: Anti-IL-1RAcPL Antibody, a Potent Antagonist of IL-18", The Journal of Immunology, vol. 165, No. 9, pp. 4950-4956, Nov. 1, 2000.

* cited by examiner (A)

(B)

(A)

(B)

(A)

(B)

(A)

Cyclin D1

(B)

(A)

(B)

SEQUENCE LISTING

```
<160> NUMBER OF SEQ ID NOS: 10

<210> SEQ ID NO 1
<211> LENGTH: 541
<212> TYPE: PRT
<213> ORGANISM: human

<400> SEQUENCE: 1

Met Asn Cys Arg Glu Leu Pro Leu Thr Leu Trp Val Leu Ile Ser Val
 1               5                  10                  15

Ser Thr Ala Glu Ser Cys Thr Ser Arg Pro His Ile Thr Val Val Glu
            20                  25                  30

Gly Glu Pro Phe Tyr Leu Lys His Cys Ser Cys Ser Leu Ala His Glu
        35                  40                  45

Ile Glu Thr Thr Thr Lys Ser Trp Tyr Lys Ser Ser Gly Ser Gln Glu
    50                  55                  60

His Val Glu Leu Asn Pro Arg Ser Ser Ser Arg Ile Ala Leu His Asp
65                  70                  75                  80

Cys Val Leu Glu Phe Trp Pro Val Glu Leu Asn Asp Thr Gly Ser Tyr
                85                  90                  95

Phe Phe Gln Met Lys Asn Tyr Thr Gln Lys Trp Lys Leu Asn Val Ile
            100                 105                 110

Arg Arg Asn Lys His Ser Cys Phe Thr Glu Arg Gln Val Thr Ser Lys
        115                 120                 125

Ile Val Glu Val Lys Lys Phe Phe Gln Ile Thr Cys Glu Asn Ser Tyr
    130                 135                 140

Tyr Gln Thr Leu Val Asn Ser Thr Ser Leu Tyr Lys Asn Cys Lys Lys
145                 150                 155                 160

Leu Leu Leu Glu Asn Asn Lys Asn Pro Thr Ile Lys Lys Asn Ala Glu
                165                 170                 175

Phe Glu Asp Gln Gly Tyr Tyr Ser Cys Val His Phe Leu His His Asn
            180                 185                 190

Gly Lys Leu Phe Asn Ile Thr Lys Thr Phe Asn Ile Thr Ile Val Glu
        195                 200                 205

Asp Arg Ser Asn Ile Val Pro Val Leu Leu Gly Pro Lys Leu Asn His
    210                 215                 220

Val Ala Val Glu Leu Gly Lys Asn Val Arg Leu Asn Cys Ser Ala Leu
225                 230                 235                 240

Leu Asn Glu Glu Asp Val Ile Tyr Trp Met Phe Gly Glu Glu Asn Gly
                245                 250                 255

Ser Asp Pro Asn Ile His Glu Glu Lys Glu Met Arg Ile Met Thr Pro
            260                 265                 270
```

```
Glu Gly Lys Trp His Ala Ser Lys Val Leu Arg Ile Glu Asn Ile Gly
            275                 280                 285

Glu Ser Asn Leu Asn Val Leu Tyr Asn Cys Thr Val Ala Ser Thr Gly
        290                 295                 300

Gly Thr Asp Thr Lys Ser Phe Ile Leu Val Arg Lys Ala Asp Met Ala
305                 310                 315                 320

Asp Ile Pro Gly His Val Phe Thr Arg Gly Met Ile Ile Ala Val Leu
                325                 330                 335

Ile Leu Val Ala Val Val Cys Leu Val Thr Val Cys Val Ile Tyr Arg
            340                 345                 350

Val Asp Leu Val Leu Phe Tyr Arg His Leu Thr Arg Arg Asp Glu Thr
        355                 360                 365

Leu Thr Asp Gly Lys Thr Tyr Asp Ala Phe Val Ser Tyr Leu Lys Glu
    370                 375                 380

Cys Arg Pro Glu Asn Gly Glu Glu His Thr Phe Ala Val Glu Ile Leu
385                 390                 395                 400

Pro Arg Val Leu Glu Lys His Phe Gly Tyr Lys Leu Cys Ile Phe Glu
                405                 410                 415

Arg Asp Val Val Pro Gly Gly Ala Val Val Asp Glu Ile His Ser Leu
            420                 425                 430

Ile Glu Lys Ser Arg Arg Leu Ile Ile Val Leu Ser Lys Ser Tyr Met
        435                 440                 445

Ser Asn Glu Val Arg Tyr Glu Leu Glu Ser Gly Leu His Glu Ala Leu
    450                 455                 460

Val Glu Arg Lys Ile Lys Ile Ile Leu Ile Glu Phe Thr Pro Val Thr
465                 470                 475                 480

Asp Phe Thr Phe Leu Pro Gln Ser Leu Lys Leu Leu Lys Ser His Arg
                485                 490                 495

Val Leu Lys Trp Lys Ala Asp Lys Ser Leu Ser Tyr Asn Ser Arg Phe
            500                 505                 510

Trp Lys Asn Leu Leu Tyr Leu Met Pro Ala Lys Thr Val Lys Pro Gly
        515                 520                 525

Arg Asp Glu Pro Glu Val Leu Pro Val Leu Ser Glu Ser
    530                 535                 540

<210> SEQ ID NO 2
<211> LENGTH: 537
<212> TYPE: PRT
<213> ORGANISM: mouse

<400> SEQUENCE: 2

Met His His Glu Glu Leu Ile Leu Thr Leu Cys Ile Leu Ile Val Lys
1               5                   10                  15

Ser Ala Ser Lys Ser Cys Ile His Arg Ser Gln Ile His Val Val Glu
            20                  25                  30

Gly Glu Pro Phe Tyr Leu Lys Pro Cys Gly Ile Ser Ala Pro Val His
        35                  40                  45

Arg Asn Glu Thr Ala Thr Met Arg Trp Phe Lys Gly Ser Ala Ser His
    50                  55                  60

Glu Tyr Arg Glu Leu Asn Asn Arg Ser Ser Pro Arg Val Thr Phe His
65                  70                  75                  80

Asp His Thr Leu Glu Phe Trp Pro Val Glu Met Glu Asp Glu Gly Thr
                85                  90                  95

Tyr Ile Ser Gln Val Gly Asn Asp Arg Arg Asn Trp Thr Leu Asn Val
```

```
            100             105             110
Thr Lys Arg Asn Lys His Ser Cys Phe Ser Asp Lys Leu Val Thr Ser
            115             120             125
Arg Asp Val Glu Val Asn Lys Ser Leu His Ile Thr Cys Lys Asn Pro
130             135             140
Asn Tyr Glu Glu Leu Ile Gln Asp Thr Trp Leu Tyr Lys Asn Cys Lys
145             150             155             160
Glu Ile Ser Lys Thr Pro Arg Ile Leu Lys Asp Ala Glu Phe Gly Asp
                165             170             175
Glu Gly Tyr Tyr Ser Cys Val Phe Ser Val His His Asn Gly Thr Arg
            180             185             190
Tyr Asn Ile Thr Lys Thr Val Asn Ile Thr Val Ile Glu Gly Arg Ser
            195             200             205
Lys Val Thr Pro Ala Ile Leu Gly Pro Lys Cys Glu Lys Val Gly Val
210             215             220
Glu Leu Gly Lys Asp Val Glu Leu Asn Cys Ser Ala Ser Leu Asn Lys
225             230             235             240
Asp Asp Leu Phe Tyr Trp Ser Ile Arg Lys Glu Asp Ser Ser Asp Pro
                245             250             255
Asn Val Gln Glu Asp Arg Lys Glu Thr Thr Thr Trp Ile Ser Glu Gly
            260             265             270
Lys Leu His Ala Ser Lys Ile Leu Arg Phe Gln Lys Ile Thr Glu Asn
            275             280             285
Tyr Leu Asn Val Leu Tyr Asn Cys Thr Val Ala Asn Glu Glu Ala Ile
            290             295             300
Asp Thr Lys Ser Phe Val Leu Val Arg Lys Glu Ile Pro Asp Ile Pro
305             310             315             320
Gly His Val Phe Thr Gly Gly Val Thr Val Leu Val Leu Ala Ser Val
                325             330             335
Ala Ala Val Cys Ile Val Ile Leu Cys Val Ile Tyr Lys Val Asp Leu
            340             345             350
Val Leu Phe Tyr Arg Arg Ile Ala Glu Arg Asp Glu Thr Leu Thr Asp
            355             360             365
Gly Lys Thr Tyr Asp Ala Phe Val Ser Tyr Leu Lys Glu Cys His Pro
            370             375             380
Glu Asn Lys Glu Glu Tyr Thr Phe Ala Val Glu Thr Leu Pro Arg Val
385             390             395             400
Leu Glu Lys Gln Phe Gly Tyr Lys Leu Cys Ile Phe Glu Arg Asp Val
                405             410             415
Val Pro Gly Gly Ala Val Val Glu Glu Ile His Ser Leu Ile Glu Lys
            420             425             430
Ser Arg Arg Leu Ile Ile Val Leu Ser Gln Ser Tyr Leu Thr Asn Gly
            435             440             445
Ala Arg Arg Glu Leu Glu Ser Gly Leu His Glu Ala Leu Val Glu Arg
            450             455             460
Lys Ile Lys Ile Ile Leu Ile Glu Phe Thr Pro Ala Ser Asn Ile Thr
465             470             475             480
Phe Leu Pro Pro Ser Leu Lys Leu Leu Lys Ser Tyr Arg Val Leu Lys
                485             490             495
Trp Arg Ala Asp Ser Pro Ser Met Asn Ser Arg Phe Trp Lys Asn Leu
            500             505             510
Val Tyr Leu Met Pro Ala Lys Ala Val Lys Pro Trp Arg Glu Glu Ser
            515             520             525
```

```
Glu Ala Arg Ser Val Leu Ser Ala Pro
    530                 535
```

<210> SEQ ID NO 3
<211> LENGTH: 599
<212> TYPE: PRT
<213> ORGANISM: human

<400> SEQUENCE: 3

```
Met Leu Cys Leu Gly Trp Ile Phe Leu Trp Leu Val Ala Gly Glu Arg
  1               5                  10                  15

Ile Lys Gly Phe Asn Ile Ser Gly Cys Ser Thr Lys Lys Leu Leu Trp
             20                  25                  30

Thr Tyr Ser Thr Arg Ser Glu Glu Phe Val Leu Phe Cys Asp Leu
         35                  40                  45

Pro Glu Pro Gln Lys Ser His Phe Cys His Arg Asn Arg Leu Ser Pro
     50                  55                  60

Lys Gln Val Pro Glu His Leu Pro Phe Met Gly Ser Asn Asp Leu Ser
 65                  70                  75                  80

Asp Val Gln Trp Tyr Gln Gln Pro Ser Asn Gly Asp Pro Leu Glu Asp
                 85                  90                  95

Ile Arg Lys Ser Tyr Pro His Ile Ile Gln Asp Lys Cys Thr Leu His
            100                 105                 110

Phe Leu Thr Pro Gly Val Asn Asn Ser Gly Ser Tyr Ile Cys Arg Pro
        115                 120                 125

Lys Met Ile Lys Ser Pro Tyr Asp Val Ala Cys Cys Val Lys Met Ile
    130                 135                 140

Leu Glu Val Lys Pro Gln Thr Asn Ala Ser Cys Glu Tyr Ser Ala Ser
145                 150                 155                 160

His Lys Gln Asp Leu Leu Leu Gly Ser Thr Gly Ser Ile Ser Cys Pro
                165                 170                 175

Ser Leu Ser Cys Gln Ser Asp Ala Gln Ser Pro Ala Val Thr Trp Tyr
            180                 185                 190

Lys Asn Gly Lys Leu Leu Ser Val Glu Arg Ser Asn Arg Ile Val Val
        195                 200                 205

Asp Glu Val Tyr Asp Tyr His Gln Gly Thr Tyr Val Cys Asp Tyr Thr
    210                 215                 220

Gln Ser Asp Thr Val Ser Ser Trp Thr Val Arg Ala Val Val Gln Val
225                 230                 235                 240

Arg Thr Ile Val Gly Asp Thr Lys Leu Lys Pro Asp Ile Leu Asp Pro
                245                 250                 255

Val Glu Asp Thr Leu Glu Val Glu Leu Gly Lys Pro Leu Thr Ile Ser
            260                 265                 270

Cys Lys Ala Arg Phe Gly Phe Glu Arg Val Phe Asn Pro Val Ile Lys
        275                 280                 285

Trp Tyr Ile Lys Asp Ser Asp Leu Glu Trp Glu Val Ser Val Pro Glu
    290                 295                 300

Ala Lys Ser Ile Lys Ser Thr Leu Lys Asp Glu Ile Ile Glu Arg Asn
305                 310                 315                 320

Ile Ile Leu Glu Lys Val Thr Gln Arg Asp Leu Arg Arg Lys Phe Val
                325                 330                 335

Cys Phe Val Gln Asn Ser Ile Gly Asn Thr Thr Gln Ser Val Gln Leu
            340                 345                 350

Lys Glu Lys Arg Gly Val Val Leu Leu Tyr Ile Leu Leu Gly Thr Ile
```

-continued

```
                355                 360                 365
Gly Thr Leu Val Ala Val Leu Ala Ala Ser Ala Leu Leu Tyr Arg His
        370                 375                 380

Trp Ile Glu Ile Val Leu Leu Tyr Arg Thr Tyr Gln Ser Lys Asp Gln
385                 390                 395                 400

Thr Leu Gly Asp Lys Lys Asp Phe Asp Ala Phe Val Ser Tyr Ala Lys
                405                 410                 415

Trp Ser Ser Phe Pro Ser Glu Ala Thr Ser Ser Leu Ser Glu Glu His
                420                 425                 430

Leu Ala Leu Ser Leu Phe Pro Asp Val Leu Glu Asn Lys Tyr Gly Tyr
                435                 440                 445

Ser Leu Cys Leu Leu Glu Arg Asp Val Ala Pro Gly Gly Val Tyr Ala
        450                 455                 460

Glu Asp Ile Val Ser Ile Ile Lys Arg Ser Arg Arg Gly Ile Phe Ile
465                 470                 475                 480

Leu Ser Pro Asn Tyr Val Asn Gly Pro Ser Ile Phe Glu Leu Gln Ala
                485                 490                 495

Ala Val Asn Leu Ala Leu Asp Asp Gln Thr Leu Lys Leu Ile Leu Ile
                500                 505                 510

Lys Phe Cys Tyr Phe Gln Glu Pro Glu Ser Leu Pro His Leu Val Lys
                515                 520                 525

Lys Ala Leu Arg Val Leu Pro Thr Val Thr Trp Arg Gly Leu Lys Ser
        530                 535                 540

Val Pro Pro Asn Ser Arg Phe Trp Ala Lys Met Arg Tyr His Met Pro
545                 550                 555                 560

Val Lys Asn Ser Gln Gly Phe Thr Trp Asn Gln Leu Arg Ile Thr Ser
                565                 570                 575

Arg Ile Phe Gln Trp Lys Gly Leu Ser Arg Thr Glu Thr Thr Gly Arg
                580                 585                 590

Ser Ser Gln Pro Lys Glu Trp
        595
```

<210> SEQ ID NO 4
<211> LENGTH: 614
<212> TYPE: PRT
<213> ORGANISM: mouse

<400> SEQUENCE: 4

```
Met Leu Cys Leu Gly Trp Val Phe Leu Trp Phe Val Ala Gly Glu Lys
1               5                   10                  15

Thr Thr Gly Phe Asn His Ser Ala Cys Ala Thr Lys Lys Leu Leu Trp
                20                  25                  30

Thr Tyr Ser Ala Arg Gly Ala Glu Asn Phe Val Leu Phe Cys Asp Leu
        35                  40                  45

Gln Glu Leu Gln Glu Gln Lys Phe Ser His Ala Ser Gln Leu Ser Pro
        50                  55                  60

Thr Gln Ser Pro Ala His Lys Pro Cys Ser Gly Ser Gln Lys Asp Leu
65                  70                  75                  80

Ser Asp Val Gln Trp Tyr Met Gln Pro Arg Ser Gly Ser Pro Leu Glu
                85                  90                  95

Glu Ile Ser Arg Asn Ser Pro His Met Gln Ser Glu Gly Met Leu His
                100                 105                 110

Ile Leu Ala Pro Gln Thr Asn Ser Ile Trp Ser Tyr Ile Cys Arg Pro
        115                 120                 125
```

-continued

```
Arg Ile Arg Ser Pro Gln Asp Met Ala Cys Cys Ile Lys Thr Val Leu
    130                 135                 140
Glu Val Lys Pro Gln Arg Asn Val Ser Cys Gly Asn Thr Ala Gln Asp
145                 150                 155                 160
Glu Gln Val Leu Leu Gly Ser Thr Gly Ser Ile His Cys Pro Ser
                165                 170                 175
Leu Ser Cys Gln Ser Asp Val Gln Ser Pro Glu Met Thr Trp Tyr Lys
                180                 185                 190
Asp Gly Arg Leu Leu Pro Glu His Lys Lys Asn Pro Ile Glu Met Ala
                195                 200                 205
Asp Ile Tyr Val Phe Asn Gln Gly Leu Tyr Val Cys Asp Tyr Thr Gln
210                 215                 220
Ser Asp Asn Val Ser Ser Trp Thr Val Arg Ala Val Lys Val Arg
225                 230                 235                 240
Thr Ile Gly Lys Asp Ile Asn Val Lys Pro Glu Ile Leu Asp Pro Ile
                245                 250                 255
Thr Asp Thr Leu Asp Val Glu Leu Gly Lys Pro Leu Thr Leu Pro Cys
            260                 265                 270
Arg Val Gln Phe Gly Phe Gln Arg Leu Ser Lys Pro Val Ile Lys Trp
            275                 280                 285
Tyr Val Lys Glu Ser Thr Gln Glu Trp Glu Met Ser Val Phe Glu Glu
    290                 295                 300
Lys Arg Ile Gln Ser Thr Phe Lys Asn Glu Val Ile Glu Arg Thr Ile
305                 310                 315                 320
Phe Leu Arg Glu Val Thr Gln Arg Asp Leu Ser Arg Lys Phe Val Cys
                325                 330                 335
Phe Ala Gln Asn Ser Ile Gly Asn Thr Thr Arg Thr Ile Arg Leu Arg
                340                 345                 350
Lys Lys Glu Glu Val Val Phe Val Tyr Ile Leu Leu Gly Thr Ala Leu
            355                 360                 365
Met Leu Val Gly Val Leu Val Ala Ala Ala Phe Leu Tyr Trp Tyr Trp
    370                 375                 380
Ile Glu Val Val Leu Leu Cys Arg Thr Tyr Lys Asn Lys Asp Glu Thr
385                 390                 395                 400
Leu Gly Asp Lys Lys Glu Phe Asp Ala Phe Val Ser Tyr Ser Asn Trp
                405                 410                 415
Ser Ser Pro Glu Thr Asp Ala Val Gly Ser Leu Ser Glu Glu His Leu
                420                 425                 430
Ala Leu Asn Leu Phe Pro Glu Val Leu Glu Asp Thr Tyr Gly Tyr Arg
            435                 440                 445
Leu Cys Leu Leu Asp Arg Asp Val Thr Pro Gly Gly Val Tyr Ala Asp
    450                 455                 460
Asp Ile Val Ser Ile Ile Lys Lys Ser Arg Arg Gly Ile Phe Ile Leu
465                 470                 475                 480
Ser Pro Ser Tyr Leu Asn Gly Pro Arg Val Phe Glu Leu Gln Ala Ala
                485                 490                 495
Val Asn Leu Ala Leu Val Asp Gln Thr Leu Lys Leu Ile Leu Ile Lys
                500                 505                 510
Phe Cys Ser Phe Gln Glu Pro Glu Ser Leu Pro Tyr Leu Val Lys Lys
            515                 520                 525
Ala Leu Arg Val Leu Pro Thr Val Thr Trp Lys Gly Leu Lys Ser Val
    530                 535                 540
His Ala Ser Ser Arg Phe Trp Thr Gln Ile Arg Tyr His Met Pro Val
```

```
                545                 550                 555                 560
Lys Asn Ser Asn Arg Phe Met Phe Asn Gly Leu Arg Ile Phe Leu Lys
                    565                 570                 575
Gly Phe Ser Pro Glu Lys Asp Leu Val Thr Gln Lys Pro Leu Glu Gly
            580                 585                 590
Met Pro Lys Ser Gly Asn Asp His Gly Ala Gln Asn Leu Leu Leu Tyr
        595                 600                 605
Ser Asp Gln Lys Arg Cys
        610

<210> SEQ ID NO 5
<211> LENGTH: 21
<212> TYPE: PRT
<213> ORGANISM: human

<400> SEQUENCE: 5

Phe Thr Glu Arg Gln Val Thr Ser Lys Ile Val Glu Val Lys Lys Phe
1               5                   10                  15
Phe Gln Ile Thr Cys
            20

<210> SEQ ID NO 6
<211> LENGTH: 21
<212> TYPE: PRT
<213> ORGANISM: human

<400> SEQUENCE: 6

Asn Ser Tyr Tyr Gln Thr Leu Val Asn Ser Thr Ser Leu Tyr Lys Asn
1               5                   10                  15
Cys Lys Lys Leu Leu
            20

<210> SEQ ID NO 7
<211> LENGTH: 18
<212> TYPE: PRT
<213> ORGANISM: mouse

<400> SEQUENCE: 7

Ser Gln Val Gly Asn Asp Arg Arg Asn Trp Thr Leu Asn Val Thr Lys
1               5                   10                  15
Arg Asn

<210> SEQ ID NO 8
<211> LENGTH: 19
<212> TYPE: PRT
<213> ORGANISM: mouse

<400> SEQUENCE: 8

Asp Ser Ser Asp Pro Asn Val Gln Glu Asp Arg Lys Glu Thr Thr Thr
1               5                   10                  15
Trp Ile Ser

<210> SEQ ID NO 9
<211> LENGTH: 22
<212> TYPE: PRT
<213> ORGANISM: human

<400> SEQUENCE: 9

Asn Ile Ser Gly Cys Ser Thr Lys Lys Leu Leu Trp Thr Tyr Ser Thr
1               5                   10                  15
```

```
Arg Ser Glu Glu Glu Phe
            20

<210> SEQ ID NO 10
<211> LENGTH: 27
<212> TYPE: PRT
<213> ORGANISM: mouse

<400> SEQUENCE: 10

Asp Leu Leu Leu Gly Ser Thr Gly Ser Ile Ser Cys Pro Ser Leu Ser
 1               5                  10                  15

Cys Gln Ser Asp Ala Gln Ser Pro Ala Val Thr
            20                  25
```

IL-18 RECEPTOR ANTAGONIST AND PHARMACEUTICAL COMPOSITION CONTAINING THE ANTAGONIST

This application is a U.S. national stage of International Application No. PCT/JP2005/013167 filed Jul. 15, 2005.

TECHNICAL FIELD

The present invention relates to an interleukin-18 receptor antagonist and a pharmaceutical composition comprising the antagonist. More specifically, the present invention relates to a pharmaceutical composition for preventing and/or treating an interleukin-18-related disorder, particularly skin thickening due to ultraviolet, which comprises an antibody against the interleukin-18 receptor α subunit and/or an antibody against the β subunit, and a pharmaceutical composition for treating a stress-related disease.

BACKGROUND ART

Skin disorders due to ultraviolet are attracting attention both from the viewpoint of aesthetics and from the viewpoint of cancer control. Epithelial keratinized cells (keratinocytes), which account for the majority of the epithelium, are observed to have abnormalities in the growth and/or differentiation thereof in various dermatitides that occur as complications in psoriasis, ichthyosis, collagen disease and the like. From this fact, it is thought that controlling the growth and/or differentiation of keratinocytes is extremely important to the health of living organisms.

The skin is an organ configured by the epidermis, which consists of overlain epithelial cells, and the dermis, which consists of dense connective tissue, forming the barrier between the outer environment and the inside of the body. The epidermis is a tissue about 1 mm in thickness that forms the outermost layer of the skin, being in direct contact with the atmosphere and protecting the inside of the skin against various stimuli (for example, solar rays, dryness, dust and the like).

The upper layer of the human skin, which confers elasticity and the barrier characteristic to the skin, that is, the epidermis, consists of four cell types defined by distinct differentiation stages (basal cell layer, which is the border of the junction between the dermis and the epidermis, prickle cell layer, granular layer, and keratinized layer).

Of the cells that constitute the epidermis, 80% are keratinized cells (keratinocytes). Keratinocytes, which have the capability of cell division, are present in the basal cell layer and move to the prickle cell layer, granular layer, and keratinized layer with the progress of differentiation. Terminal cells of the corneal layer, which are called corneocytes, are already dead. The epidermis is a constantly renewed tissue, and the program for cell cleavage and progress to finally differentiated corneocytes is very strictly controlled. In the basal cell layer, cell division occurs constantly; the resulting cells move while changing the shape thereof, and about 28 days later, they drop off from the corneal layer as dirt.

As such, the differentiation of the epidermis, which turns over in a 28-day cycle, is important to the conferment of the essential function of the skin, that is, the conferment of the protective barrier against the outer environment, and the prevention of the loss of water from the body.

The skin is sensitively influenced by temperature/humidity, ultraviolet, cosmetics, aging, disease, stress, dietary habits and the like; as a result, various troubles, including deterioration of the above-described skin functions and skin senescence, occur.

Ultraviolet (UV) has a sterilizing action and has effects of promoting bone formation by vitamin D and improving the immune function of the skin, and on the other hand produces skin thickening, wrinkle or pouch formation, pigmentation and the like.

As acute reactions due to ultraviolet in the skin, sunburns and photosensitive dermatitis can be mentioned; as chronic reactions, skin pigment abnormalities (exacerbation of stains and freckles) and promotion of skin senescence can be mentioned. When the skin is exposed to ultraviolet, an enzyme system of the arachidonic acid cycle is induced in skin cells, resulting in the generation of prostaglandin E2. Prostaglandin E2 has a function to inflame skin cells, causing red swelling (erythema) and sunburns. Sunburns in turn cause stains and thicken epidermal cells. As such, epidermal thickening leads to the onset of skin cancer.

Because epidermal thickening is an abnormal growth of keratinocytes, epidermal thickening can be suppressed by suppressing this growth to promote the differentiation thereof.

As major attempts to prevent or ameliorate troubles that occur in the skin, a method of preventing the dryness of the skin and increasing the moisture retention potential of the skin by applying a synthetic or natural moisturizer, a method of improving blood flow by applying a blood circulation promoter, and the like have been performed.

However, these methods pose various problems in terms of prophylactic and ameliorating effects on various skin troubles, the persistency thereof, drug stability and safety, and the like. Specifically, because these methods are generally to replenish water in the epidermis, particularly in the corneal surface, or to supplement part of moisturizer, the indications and effects thereof are transient so that a permanent amelioration of the skin has been unexpectable.

Hence, there is a demand for the development of a substance having a remarkable suppressive action on epidermal thickening, insufficient keratinization of the skin, lipid metabolism abnormalities and the like.

Generally, the growth or differentiation of cells requires a particular growth factor or differentiation factor. Also, the immune responses exhibited by living organisms to bacterial and/or viral infections, tumors and cytotoxicity are regulated by direct or indirect interactions between immunocompetent cells. Cytokines (for example, interleukins, colony stimulating factors, TNFs (tumor necrosis factors), interferons) have been shown to be involved in the differentiation, growth and immune responses of cells.

Interleukin-18 (IL-18) was identified as a novel protein that induces the production of IFN-γ in immunocompetent cells (see, for example, patent document 1). Currently, IL-18 is known to induce not only the production of interferon-γ, which is an inflammatory cytokine, but also the production of anti-inflammatory cytokines (for example, interleukin-4, interleukin-5, and interleukin-13) (see, for example, non-patent document 1).

IL-18 protein is produced as the 24-kDa inactive form (precursor) and cleaved by caspase-1 into the 18-kDa active form, after which it is released out of the cells (see, for example, non-patent document 4). In cultured cells, the IL-18 precursor is expressed in activated macrophages, cerebral microglia, keratinized cells of the skin, Langerhans' cells, corneal epithelial cells, intestinal epithelial cells, uterine gland cells, osteoblasts and the like (see, for example, non-patent document 5). Also, IL-18 protein is known to increase locally in lesions in Alzheimer's disease, Sjoegren's syndrome, Crohn's disease, osteoarthritis, rheumatic arthritis, contact dermatitis, psoriasis, atherosclerosis, and the like (see, for example, non-patent document 6).

IL-18 receptor consists of the α subunit and the β subunit (see, for example, non-patent document 7), and is classified in the IL-1β receptor/TLR family based on the amino acid sequence thereof (see, for example, non-patent documents 5, 6, and 8). The IL-18 activated form protein is known to elevate NF-κB-dependent transcriptional activity and AP-1-dependent transcriptional activity via the IL-18 receptors (see, for example, non-patent document 5). The latter is known to be involved by JNK and p38 MAPK (see, for example, non-patent document 9). The mRNA of the IL-18 receptor α subunit is expressed in the brain, thymus, uterus, adrenal, liver, pancreas, lung, spleen, skeletal muscle, NK cells, T cells and the like (see, for example, non-patent document 6).

Regarding the relationship between IL-18 and disease, it is known that in schizophrenia, neonatal brain hypoplasia, panic disorder, multiple sclerosis, systemic lupus erythematosus (SLE), allergic asthma, hyperthyroidism, type I diabetes mellitus, liver cirrhosis, renal insufficiency, septicemia, atopic dermatitis, premature amniorrhexis, HIV infection, malaria infection and the like, IL-18 protein in patient serum exhibits high values (see, for example, non-patent document 6), and that in patients with endometriosis in chronic stage, the IL-18 protein concentration in ascitic fluid rises (see, for example, non-patent document 10). According to an analysis using animal models, in models of multiple sclerosis or rheumatic arthritis, IL-18 administration worsens the condition, whereas administration of an anti-IL-18 antibody ameliorates or mitigates the condition (see, for example, non-patent documents 11 and 12). On the other hand, in a model of acute graft-versus-host disease (GVHD), IL-18 administration reduces TNFα production and lowers the mortality rate, whereas administration of an anti-IL-18 antibody increases the mortality rate (see, for example, non-patent document 13).

As stated above, there is no definite relationship between IL-18 and disease. This represents the multi-functionality of IL-18, making it more difficult to understand the functions of IL-18 in living organisms.

Patent document 1: Japanese Patent Unexamined Publication No. HEI-8-27189 (published Jan. 30, 1996)

Non-patent document 1: Kyukyu Igaku, volume 26, pages 1823-1826, December 2002

Non-patent document 2: Journal of Immunology, volume 163, pages 1230-1236, 1999

Non-patent document 3: Anticancer Research, volume 19, pages 4131-4138, 1999

Non-patent document 4: Science, volume 275, pages 206-209, 1997

Non-patent document 5: Annu Rev Immunol., volume 19, pages 423-474, 2001

Non-patent document 6: The Cytokine Handbook, fourth edition (Academic Press), volume 2, pages 709-733, 2002

Non-patent document 7: J. Biol. Chem., volume 272, pages 25737-25742, 1997

Non-patent document 8: Life Sci., volume 68, pages 241-258, 2000

Non-patent document 9: Biochem. Biophys. Res. Commun., volume 296, pages 742-748, 2002

Non-patent document 10: Fertil. Steril., volume 80, pages 889-894, 2003

Non-patent document 11: J. Immunol., volume 161, pages 6368-6374, 1998

Non-patent document 12: J. Clin. Invest., volume 104, pages 1337-1339, 1999

Non-patent document 13: J. Exp. Med., volume 194, pages 1433-1440, 2001

DISCLOSURE OF THE INVENTION

Problems to Be Solved by the Invention

The present inventors found that when activated form IL-18 was added to the culture medium of keratinocytes cultured at high density, contact inhibition was blocked, which led to the overgrowth of the cells. Furthermore, the present inventors found that when IL-18 was added to the culture supernatant of differentiation-induced cultured keratinocytes, the differentiation thereof was promoted, and that when an anti-IL-18 antibody was further added, this promotion of differentiation was suppressed. Hence, the present inventors found that IL-18 was capable of controlling epidermal thickening by being involved in the growth and/or differentiation of keratinocytes.

However, currently available antibodies against the IL-18 receptors cannot be used for immunohistochemistry, tissues in which a receptor protein is actually expressed are unknown, and it is difficult to confirm that IL-18 functions actually in a living organism. The research into the expression of the IL-18 receptors that has been conducted to date is to analyze the expression at the nucleic acid level, and does not clearly show in which tissues an IL-18 receptor protein is expressed actually.

The present invention has been developed in view of the above-described problems, and is intended to provide an IL-18 receptor antibody that functions as an IL-18 receptor antagonist and is usable for immunohistochemistry. In other words, an object of the present invention is to supply an antibody that binds to an IL-18 receptor to inhibit a function of IL-18 in a living organism, and to prevent and/or treat an IL-18-dependent disorder, particularly skin thickening caused by ultraviolet, using the antibody.

Furthermore, the present inventors found that the blood IL-6 level rose due to the stress-dependent elevation of blood IL-18 level, and that as a result, the pathology/condition of stress-related disease exacerbated. Based on this finding, an object of the present invention is to supply an antibody that binds to an IL-18 receptor to inhibit a function of IL-18 in a living organism, and to treat or prevent an IL-18/IL-6-dependent disorder, particularly a stress-related disease, using the antibody.

Means of Solving the Problems

The present inventors prepared anti-IL-18 receptor antibodies that function as IL-18 receptor antagonists and are usable for immunohistochemistry, for the purpose of examining the functions of IL-18. Specifically, the present inventors prepared polyclonal antibodies against the two subunits of the IL-18 receptor (anti-α antibody and anti-β antibody), using the hydrophilic domains in the vicinities of the transmembrane regions of the IL-18 receptor α subunit and β subunit as the antigens.

An antibody according to the present invention is characterized by binding to an IL-18 receptor.

In the antibody according to the present invention, the above-described IL-18 receptor is preferably the α subunit.

In the antibody according to the present invention, the amino acid sequence of the above-described IL-18 receptor α subunit to which the antibody binds is preferably the amino acid sequence shown by any of SEQ ID NO:5 to 8.

In the antibody according to the present invention, the above-described IL-18 receptor is preferably the β subunit.

In the antibody according to the present invention, the amino acid sequence of the above-described IL-18 receptor β to which the antibody binds is preferably the amino acid sequence shown by SEQ ID NO:9 or 10.

An antibody production method according to the present invention is characterized by comprising a step for eliciting an antibody, using a polypeptide consisting of the amino acid sequence shown by any of SEQ ID NO:5 to 8 as the antigen.

An antibody production method according to the present invention is characterized by comprising a step for eliciting an antibody, using a mixture of a polypeptide consisting of the amino acid sequence shown by SEQ ID NO:5 and a polypeptide consisting of the amino acid sequence shown by SEQ ID NO:6 as the antigen.

An antibody production method according to the present invention is characterized by comprising a step for eliciting an antibody, using a mixture of a polypeptide consisting of the amino acid sequence shown by SEQ ID NO:7 and a polypeptide consisting of the amino acid sequence shown by SEQ ID NO:8 as the antigen.

An antibody production method according to the present invention is characterized by comprising a step for eliciting an antibody, using a mixture of a polypeptide consisting of the amino acid sequence shown by SEQ ID NO:9 and a polypeptide consisting of the amino acid sequence shown by SEQ ID NO:10 as the antigen.

An antibody according to the present invention is preferably produced by one of the above-described production methods.

A pharmaceutical composition according to the present invention is characterized by comprising the antibody described in claim 1, 2 or 7.

A pharmaceutical composition according to the present invention is preferably used to treat or prevent an IL-18-related disorder.

In the pharmaceutical composition according to the present invention, the above-described IL-18-related disorder is preferably an IL-18/IL-6-related disorder.

In the pharmaceutical composition according to the present invention, the above-described IL-18-related disorder is preferably a stress-related disease.

In the pharmaceutical composition according to the present invention, the above-described stress-related disease is preferably selected from the group consisting of rheumatic arthritis, systemic lupus erythematosus, multiple sclerosis, acne vulgaris, Crohn's disease, ulcerative colitis, atopic dermatitis, bronchial asthma, Sjoegren's syndrome, depression, and psychosomatic disease.

In the pharmaceutical composition according to the present invention, the above-described disorder is preferably characterized by skin thickening.

In the pharmaceutical composition according to the present invention, the above-described disorder is preferably ultraviolet-dependent skin loss, hardening or thickening.

In the pharmaceutical composition according to the present invention, the above-described disorder is preferably hair growth disorders.

A pharmaceutical composition according to the present invention is preferably in a form applicable to the skin surface.

A pharmaceutical composition according to the present invention preferably further comprises a pharmaceutically acceptable excipient.

A method of enhancing the differentiation of keratinocytes in the human skin according to the present invention is characterized by comprising a step for applying one of the above-described pharmaceutical compositions to the skin.

A method of inhibiting the growth of keratinocytes in the human skin according to the present invention is characterized by comprising a step for applying one of the above-described pharmaceutical compositions to the skin.

A method of promoting hair growth according to the present invention is characterized by comprising a step for applying one of the above-described pharmaceutical compositions to the skin.

A pharmaceutical composition according to the present invention is characterized by comprising activated form IL-18 to prevent and/or treat cell death due to apoptosis.

In the pharmaceutical composition according to the present invention, the above-described cells are preferably keratinocytes.

A pharmaceutical composition according to the present invention is characterized by comprising a superoxide dismutase to prevent and/or treat an IL-18-related disorder.

A pharmaceutical composition according to the present invention is characterized by comprising a p38 MAPK inhibitor to prevent and/or treat an IL-18-related disorder.

A pharmaceutical composition according to the present invention is characterized by comprising a caspase-1 inhibitor to prevent and/or treat an IL-18-related disorder.

A pharmaceutical composition according to the present invention is characterized by comprising a caspase-11 inhibitor to prevent and/or treat an IL-18-related disorder.

In the pharmaceutical composition according to the present invention, the above-described IL-18-related disorder is preferably an IL-18/IL-6-related disorder.

In the pharmaceutical composition according to the present invention, the above-described IL-18-related disorder is preferably a stress-related disease.

EFFECT OF THE INVENTION

An antibody according to the present invention has an effect of binding to the IL-18 receptor α subunit in a living organism to inhibit a function of IL-18 (for example, production of IFN-γ). Also, an antibody according to the present invention has an effect of binding to the IL-18 receptor β subunit in a living organism to inhibit a function of IL-18 (for example, production of IFN-γ). Also, an antibody according to the present invention has an effect of being usable in all of the various experiments of immunohistochemistry on tissue specimens, flowcytometry, immunoprecipitation, Western blot, and ELISA.

A pharmaceutical composition comprising IL-18 according to the present invention has an effect of preventing and/or treating a stress-related disease. Also, a pharmaceutical composition according to the present invention has an effect of promoting keratinocyte differentiation induction and suppressing epidermal thickening. Hence, because a pharmaceutical composition according to the present invention has an action to normalize the abnormal keratinization of skin epidermic cells, it has an effect of being usable as a keratinization ameliorating agent. Furthermore, because a pharmaceutical composition according to the present invention has a remarkable suppressive action on epidermal thickening due to ultraviolet, it has an effect of being capable of restoring a normal function of the skin.

Using the present invention, the differentiation of keratinocytes can be enhanced. Also, using the present invention, the growth of keratinocytes can be inhibited. Furthermore, using the present invention, hair growth can be promoted.

Epidermal thickening is an abnormal growth of keratinocytes; particularly, ultraviolet (UV)-dependent epidermal thickening is thought to be a sign of epidermal carcinogenesis. Hence, using a pharmaceutical composition according to the present invention, by suppressing the abnormal growth of keratinocytes and promoting the differentiation thereof, epidermal thickening can be suppressed and skin cancer can be prevented and/or treated.

Using a pharmaceutical composition comprising IL-18 according to the present invention, cell death due toapoptosis can be prevented and/or treated.

BEST MODE FOR EMBODYING THE INVENTION

1: IL-18 Receptor Antagonists

Figure 1:
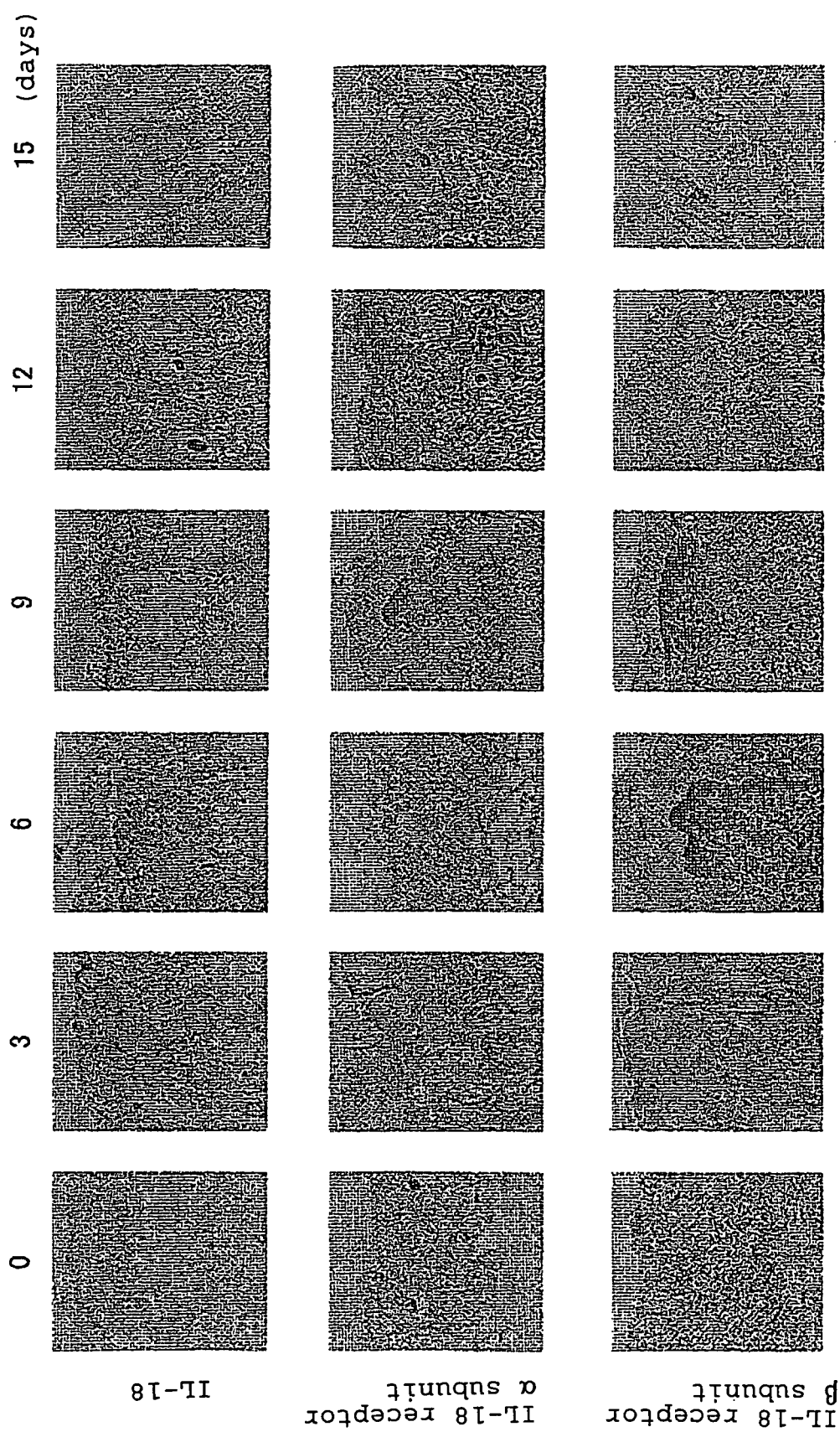
FIG. 1 presents immunohistochemical specimens showing the process of expression of IL-18 or IL-18 receptor in UV-irradiated mouse epidermis.

The present inventors investigated whether or not epidermal thickening could be controlled via the IL-18-related signal transduction pathway, using IL-18 receptor antagonists.

Specifically, the present inventors prepared antibodies against IL-18 receptors that remarkably inhibit the IL-18-dependent production of interferon-γ, and analyzed the relationship between IL-18 and epidermal thickening using these antibodies as the IL-18 receptor antagonists.

(a) IL-18 Receptor Antibodies

The present invention provides an antibody that binds specifically to the IL-18 receptor α subunit. In one mode of embodiment, the antibody of the present invention preferably binds specifically to a polypeptide consisting of the 120th to 140th positions (SEQ ID NO:5) or the 142nd to 162nd positions (SEQ ID NO:6) of the amino acid sequence of the human IL-18 receptor α subunit (GenBank accession number U43672 (SEQ ID NO:1)), or the 99th to 116th positions (SEQ ID NO:7) or the 252nd to 270th positions (SEQ ID NO:8) of the amino acid sequence of the mouse IL-18 receptor α subunit (GenBank accession number U43673 (SEQ ID NO:2)).

The present invention further provides an antibody that binds specifically to the IL-18 receptor β subunit. In one mode of embodiment, the antibody of the present invention preferably binds specifically to a polypeptide consisting of the 21st to 42nd positions (SEQ ID NO:9) or the 164th to 190th positions (SEQ ID NO:10) of the amino acid sequence of the human IL-18 receptor β subunit (GenBank accession number AF077346 (SEQ ID NO:3)).

Although an antibody according to the present invention is preferably elicited using one of the above-described peptides as the antigen, it is also preferable to use these peptides in mixture as the antigen.

As used herein, the term "antibody" means an immunoglobulin (IgA, IgD, IgE, IgG, IgM and Fab fragments, F(ab')$_2$ fragments, and Fc fragments thereof); examples thereof include polyclonal antibodies, monoclonal antibodies, single-chain antibodies, anti-ideotype antibodies and humanized antibodies, but are not limited thereto. An antibody according to the present invention can be useful in selecting a biological material that expresses an IL-18 receptor.

An "antibody" can be prepared according to various known methods (for example, HarLow et al., "Antibodies: A laboratory manual, Cold Spring Harbor Laboratory, New York (1988)", Iwasaki et al., "Monoclonal antibody hybridomas and ELISA, Kodansha (1991)").

A peptide antibody is prepared by a method widely known in the relevant field. See, for example, Chow, M. et al., Proc. Natl. Acad. Sci. USA 82: 910-914; and Bittle, F. J. et al., J. Gen. Virol. 66: 2347-2354 (1985) (herein cited for the sake of reference). Generally, an animal can be immunized with a free peptide; however, an anti-peptide antibody titer can be boosted by coupling the peptide to a polymeric carrier (for example, keyhole limpet hemocyanin (KLH) or tetanus toxoid). For example, a cysteine-containing peptide can be coupled to a carrier using a linker like m-maleimidobenzoyl-N-hydroxysuccinimide ester (MBS), whereas other peptides can be coupled to a carrier using a more common linking agent like glutaraldehyde. Animals like rabbits, rats, and mice can be immunized with any of a free or carrier-coupled peptide by, for example, intraperitoneal and/or intradermal injection of an emulsion comprising about 100 μg of peptide or carrier protein and Freund's adjuvant. Some booster injections can be required at intervals of, for example, about 2 weeks, in order to provide, for example, an anti-peptide antibody of useful titer that can be detected by ELISA assay using a free peptide adsorbed to a solid surface. The titer of the anti-peptide antibody in serum from an immunized animal can be increased by choosing an anti-peptide antibody, for example, using adsorption to the peptide on a solid support and elution of the antibody chosen by a method widely known in the relevant field.

As used herein, the term "antibody that binds specifically to an IL-18 receptor" encompasses that a complete antibody molecule and antibody fragment (for example, Fab and F(ab')$_2$ fragments) capable of binding specifically to an IL-18 receptor. The term "IL-18 receptor", unless otherwise stated herein, is intended to mean both or either of the α subunit and β subunit of the receptor. The Fab and F(ab')$_2$ fragments lack the Fc portion of the complete antibody, is more quickly eliminated by circulation, and can hardly have the nonspecific tissue binding of the complete antibody (Wahl et al., J. Nucl. Med. 24: 316-325 (1983) (herein cited for the sake of reference)). Therefore, these fragments are preferable.

Furthermore, an additional antibody capable of binding to a peptide antigen of an IL-18 receptor can be produced by 2-step procedures through the use of an anti-ideotype antibody. Such a method utilizes the fact that an antibody per se is an antigen, and therefore enables to obtain an antibody that binds to a secondary antibody. According to this method, an antibody that binds specifically to an IL-18 receptor is used to immunize an animal (preferably a mouse). Next, splenocytes of such an animal are used to produce hybridoma cells, and the hybridoma cells are screened to identify a clone that produces an antibody whose capability of binding to an antibody that binds specifically to an IL-18 receptor can be blocked by an IL-18 receptor peptide antigen. Such antibodies include anti-ideotype antibodies against an antibody that binds specifically to an IL-18 receptor, and can be used to immunize an animal for inducing the formation of an antibody that binds specifically to an additional IL-18 receptor.

It is evident that Fab and F(ab')$_2$ and other fragments of an antibody according to the present invention can be used according to a method disclosed herein. Such a fragment is produced representatively by cleavage due to proteolysis using an enzyme like papain (resulting in an Fab fragment) or pepsin (resulting in an F(ab')$_2$ fragment). Alternatively, an IL-18 receptor binding fragment can be produced by applying recombinant DNA technology or by synthetic chemistry.

Hence, it can be said that an antibody according to the present invention only need to have at least an antibody fragment that recognizes an IL-18 receptor peptide antigen according to the present invention (for example, Fab and F(ab')$_2$ fragments). Therefore, it should be noted that an immunoglobulin consisting of an antibody fragment that recognizes an IL-18 receptor peptide antigen according to the present invention and an Fc fragment of a different antibody molecule is also included in the present invention.

Hence, an object of the present invention resides in the provision of an antibody that recognizes an IL-18 receptor according to the present invention, and does not reside in the kinds of individual immunoglobulins (IgA, IgD, IgE, IgG or IgM), chimeric antibody preparation method, peptide antigen preparation method and the like described specifically herein. Therefore, it should be noted that an antibody acquired by methods other than the above-described methods is also encompassed in the scope of the present invention.

(b) Antigen Peptides

The present inventors found that a polypeptide consisting of a particular region of IL-18 receptor protein elicited an antibody usable for the immunohistochemistry of IL-18, and capable of functioning as an IL-18 receptor antagonist, and completed the present invention.

The present invention provides a polypeptide consisting of the 120th to 140th positions (SEQ ID NO:5) or the 142nd to 162nd positions (SEQ ID NO:6) of the amino acid sequence of the human IL-18 receptor α subunit (GenBank accession number U43672 (SEQ ID NO:1)), or the 99th to 116th positions (SEQ ID NO:7) or the 252nd to 270th positions (SEQ ID NO:8) of the amino acid sequence of the mouse IL-18 receptor α subunit (GenBank accession number U43673 (SEQ ID NO:2)), or a polypeptide consisting of the 21st to 42nd positions (SEQ ID NO:9) or the 164th to 190th positions (SEQ ID NO:10) of the amino acid sequence of the human IL-18 receptor β subunit (GenBank accession number AF077346 (SEQ ID NO:3)).

As used herein, the term "polypeptide" is used interchangeably with "peptide" or "protein". A polypeptide according to the present invention may also be isolated from a natural source, or produced by recombinant technology, or chemically synthesized.

The term "isolated" polypeptide or protein is intended to mean a polypeptide or protein taken out from the natural environment thereof. For example, a polypeptide and protein produced by recombinant technology, expressed in host cells, are thought to have been isolated in the same manner as a natural or recombinant polypeptide and protein substantially purified by an optionally chosen appropriate technology.

Polypeptides according to the present invention include products produced from natural purified products, products of chemical synthesis procedures, and prokaryotic hosts or eukaryotic hosts (including, for example, bacterial cells, yeast cells, higher plant cells, insect cells, and mammalian cells) by recombinant technology.

A polypeptide according to the present invention may be in a state wherein the a polynucleotide according to the present invention described below (gene that encodes a polypeptide according to the present invention) is introduced to a host cell, and the polypeptide is expressed in the cell, or may also be isolated and purified from a cell, tissue and the like. Also, a polypeptide according to the present invention may be a chemically synthesized one.

Also, a polypeptide according to the present invention may be one comprising an additional polypeptide. As examples of the additional polypeptide, polypeptides labeled with an epitope such as His, Myc, and Flag can be mentioned. In a preferred mode of embodiment, a polypeptide according to the present invention can be recombinantly expressed in an altered form like a fusion protein. For example, to improve the stability and persistency during purification or during subsequent operation and storage in host cells, a region of additional amino acids, particularly chargeable amino acids, of a polypeptide according to the present invention, can be added to the N-terminus of the polypeptide.

A synthetic peptide can be synthesized using a known method of chemical synthesis. For example, Houghten describes a simple method for the synthesis of a large number of peptides, like 10 to 20 mg of 248 different 13-residue peptides showing a single amino acid modification of the HA1 polypeptide segment, that are prepared and characterized in less than 4 weeks. Houghten, R. A., Proc. Natl. Acad. Sci. USA 82: 5131-5135 (1985). This "Simultaneous Multiple Peptide Synthesis (SMPS)" process is further described in U.S. Pat. No. 4,631,211 of Houghten et al. (1986). In this procedure, individual resins for the solid phase synthesis of various peptides are contained in separate solvent-permeable packets, and enable the optimum use of many of the same repetitive steps concerning the solid phase method. The complete manual procedures enable the simultaneous performance of 500 to 1000 or more syntheses (Houghten et al., ibidem, 5134). These documents are herein cited for the sake of reference.

A polypeptide according to the present invention is useful in a method and kit for preparing an antibody that is effective for immunohistochemistry and capable of functioning as an IL-18 receptor antagonist.

Hence, it can be said that a polypeptide according to the present invention may be any one comprising at least a peptide consisting of any one of SEQ ID NO:5 to 10. Therefore, it should be noted that a polypeptide consisting of a peptide consisting of any one of SEQ ID NO:5 to 10 and an optionally chosen amino acid sequence having a particular function (for example, tag) is also included in the present invention. Also, a peptide consisting of any one of SEQ ID NO:5 to 10 and the optionally chosen amino acid sequence may be joined via an appropriate linker peptide in a way that does not inhibit the respective functions.

Accordingly, an object of the present invention resides in the provision of a polypeptide for preparing an antibody that is useful for immunohistochemistry and capable of functioning as an IL-18 receptor antagonist, and does not reside in the polypeptide preparation methods and the like specifically described herein. Therefore, it should be noted that a polypeptide enabling the preparation of an antibody that is effective for immunohistochemistry and capable of functioning as an IL-18 receptor antagonist, acquired by methods other than the above-described methods, is also encompassed in the scope of the present invention.

(c) Polynucleotides that Encode Antigen Peptides

The present invention provides polynucleotides that encode the above-described polypeptides according to the present invention. As used herein, the term "polynucleotide" is used interchangeably with "nucleic acid" or "nucleic acid molecule", and is intended to mean a polymer of nucleotide. As used herein, the term "base sequence" is used interchangeably with "nucleic acid sequence" or "nucleotide sequence", and is shown as a sequence of deoxyribonucleotide (abbreviated as A, G, C and T).

A polynucleotide according to the present invention may be produced as a cleavage fragment of a longer polynucleotide (for example, a polynucleotide consisting of the full-length cDNA that encodes an IL-18 receptor protein), or chemically synthesized. Referring to the present description, because the base sequence shown by SEQ ID NO:2 is provided, those skilled in the art can easily prepare a DNA fragment based on SEQ ID NO:2. For example, restriction endonuclease cleavage or shearing by sonication can easily be used to prepare fragments of various sizes. Alternatively, such a fragment can be prepared synthetically. An appropriate fragment (oligonucleotide) is synthesized using the 392 model synthesizer of Applied Biosystems Incorporated (ABI, 850 Lincoln Center Dr., Foster City, Calif. 94404) and the like.

As the method of acquiring a polynucleotide according to the present invention, a method using a means of amplification such as PCR can be mentioned. For example, by preparing respective primers from among the 5' side and 3' side sequences (or complementary sequences thereto) of cDNAs of a polynucleotide in the present invention, and performing PCR and the like using these primers with a genomic DNA (or cDNA) and the like as the template to amplify the DNA region sandwiched between the two primers, a DNA fragment comprising a polynucleotide according to the present invention can be acquired in a large amount.

Also, a polynucleotide according to the present invention can be fused to a polynucleotide that encodes the above-described tag label (tag sequence or marker sequence) on the 5' side or 3' side thereof.

Accordingly, an object of the present invention resides in the provision of a polynucleotide that encodes an antigen polypeptide capable of eliciting an antibody that is effective for immunohistochemistry and capable of functioning as an IL-18 receptor antagonist, and does not reside in the polynucleotide preparation method and the like described specifically herein. Therefore, it should be noted that polynucleotides that encode the above-described polypeptides, acquired by methods other than the above-described methods, are also encompassed in the scope of the present invention.

(d) Production of Antigen Peptides

[1] Polypeptide Production Method

The present invention provides a production method for a polypeptide according to the present invention.

In one mode of embodiment, a production method for a polypeptide according to the present invention is characterized by using a vector comprising a polynucleotide that encodes a polypeptide according to the present invention.

In one aspect of this mode of embodiment, a production method for the polypeptide according to this mode of embodiment preferably employs a recombinant expression system. When a recombinant expression system is used, a method comprising inserting a polynucleotide according to the present invention to a recombinant expression vector, then introducing the vector to a host in a way that enables the expression thereof by a known method, and purifying the above-described polypeptide obtained as a result of translation in the host, and the like can be adopted. The recombinant expression vector may or may not be a plasmid, as long as it enables the introduction of the desired polynucleotide to the host. Preferably, the production method for the polypeptide according to this mode of embodiment comprises a step for introducing the above-described vector to a host.

When an exogenous polynucleotide is introduced to a host as described above, the expression vector preferably incorporates a promoter that functions in the host in a way that enables the expression of the exogenous polynucleotide. Although the method for purifying the recombinantly produced polypeptide differs depending on the host used and the properties of the polypeptide, it is possible to relatively easily purify the desired polypeptide by means of a tag and the like.

A production method for the polypeptide according to this mode of embodiment preferably further comprises a step for purifying a polypeptide according to the present invention from a cell or tissue extract comprising the polypeptide. The step for purifying the polypeptide is preferably a step for preparing a cell extract from cells or tissue by a widely known method (for example, a method comprising disrupting cells or tissue, then performing centrifugation and recovering the soluble fraction), and then purifying the polypeptide from this cell extract by a widely known method (for example, ammonium sulfate precipitation or ethanol precipitation, acid extraction, anion or cation exchange chromatography, phosphocellulose chromatography, hydrophobic interaction chromatography, affinity chromatography, hydroxyapatite chromatography, and lectin chromatography), but is not limited thereto.

In another mode of embodiment, a production method for a polypeptide according to the present invention is characterized by chemically synthesizing a polypeptide according to the present invention. Those skilled in the art easily understand that a polypeptide according to the present invention can be chemically synthesized by applying a widely known chemical synthesis technology on the basis of the amino acid sequence of a polypeptide according to the present invention described herein.

Hence, it can be said that a production method for a polypeptide according to the present invention may be any one at least using a known commonly used technology on the basis of the amino acid sequence of an IL-18 receptor protein or the base sequence of a polynucleotide that encodes an IL-18 receptor protein.

Hence, an object of the present invention resides in the provision of a production method for a polypeptide according to the present invention, and it should be noted that production methods comprising a step other than the above-described various steps are also encompassed in the scope of the present invention.

[2] Vector and Cells for Recombinant Expression

The present invention provides a vector used to produce an antigen polypeptide capable of eliciting an antibody that is effective for immunohistochemistry and capable of functioning as an IL-18 receptor antagonist. Preferably, a vector according to the present invention can be a vector used for recombinant expression.

A vector according to the present invention is not subject to limitation, as long as it comprises one of the above-described polynucleotides according to the present invention. Examples of the method of preparing a recombinant expression vector include methods using a plasmid, phage, or cosmid and the like can be mentioned, but are not limited thereto.

The specific kind of the vector is not subject to limitation, as long as a vector expressible in the host cells is chosen as appropriate. Hence, a promoter sequence is selected as appropriate to ensure the expression of a polynucleotide according to the present invention, according to the kind of the host cells, and a vector prepared by incorporating this and a polynucleotide according to the present invention into various plasmids may be used as the expression vector.

The expression vector preferably comprises at least one selection marker. As such a marker, dihydrofolate reductase or neomycin resistance for eukaryotic cell culture, and the tetracycline resistance gene or the ampicillin resistance gene for culture in *E. coli* and other bacteria, can be mentioned.

Using the above-described selection marker, it is possible to confirm whether or not a polynucleotide according to the present invention has been introduced to the host cells, and whether or not the same is accurately expressed in the host cells. Alternatively, a polypeptide according to the present invention may be expressed as a fusion polypeptide.

The above-described host cells are not subject to limitation; various conventionally known cells can be used suitably. Specifically, for example, bacteria such as *Escherichia coli*, yeasts (*Saccharomyces cerevisiae, Schizosaccharomyces pombe*), *Caenorhabditis elegans, Xenopus laevis* oocytes and the like can be mentioned, but are not limited thereto. Appropriate culture media and conditions for the above-described host cells are widely known in the relevant field.

The method for introducing the above-described expression vector into host cells, that is, the transformation method, is not subject to limitation; conventionally known methods such as electroporation, calcium phosphate method, liposome method, and DEAE dextran method can be used suitably. Also, for example, when a polypeptide according to the present invention is transfer-expressed in an insect, an expression system using baculovirus may be used.

Hence, it can be said that a vector according to the present invention may be any one comprising at least a polynucleotide that encodes a polypeptide according to the present invention. Therefore, it should be noted that vectors other than expression vectors are included in the technical scope of the present invention.

Accordingly, an object of the present invention resides in the provision of a vector comprising a polynucleotide that encodes a polypeptide according to the present invention, and does not reside in the individual vector species and cell species, as well as vector preparation methods and cell introduction methods described specifically herein. Therefore, it should be noted that vectors acquired using a vector species and vector preparation method other than those described above are also encompassed in the scope of the present invention.

The present invention further provides cells introduced a polynucleotide that encodes an antigen polypeptide capable of eliciting an antibody that is effective for immunohistochemistry and capable of functioning as an IL-18 receptor antagonist. The cell preparation method (production method) is not subject to limitation; for example, a method comprising introducing the above-described recombinant vector into a host to transform the host can be mentioned.

Confirmation of whether or not the gene has been introduced to the cell can be performed by PCR, Southern hybridization, Northern hybridization and the like. For example, DNA is prepared from transformant cells, DNA-specific primers are designed, and PCR is performed. The PCR can be performed under the same conditions as those used to prepare the aforementioned plasmid. Subsequently, by subjecting the amplification product to agarose gel electrophoresis, polyacrylamide gel electrophoresis or capillary electrophoresis and the like, staining with ethidium bromide, SYBR Green solution and the like, and detecting the amplification product as a single band, the fact of transformation can be confirmed. Also, it is possible to perform PCR using a primer previously labeled with a fluorescent dye, and to detect the amplification product. Furthermore, a method comprising binding the amplification product to a solid phase such as a microplate, and confirming the amplification product by fluorescence or an enzyme reaction and the like, can also be adopted.

An object of the present invention resides in the provision of cells introduced a polynucleotide that encodes a polypeptide according to the present invention, and does not reside in the individual vector species and introduction methods described specifically herein. Therefore, it should be noted that cells acquired using a vector species and cell species, as well as vector preparation method and cell introduction method other than those described above are also encompassed in the scope of the present invention.

2: Pharmaceutical Composition Comprising IL-18 Receptor Antagonist

The present inventors found that administration of an IL-18 receptor antagonist to the skin after ultraviolet irradiation was effective in avoiding epidermal thickening. The present inventors further found that in mouse keratinocytes showing thickening after UV irradiation, the expression levels of IL-18 (6 to 12 days after UV irradiation), IL-18 receptor α subunit (9 to 12 days after UV irradiation), and β subunit (6 to 9-days after UV irradiation) increased.

By applying an antibody that inhibits a function of IL-18 or an IL-18 receptor antagonist to a mouse at 4 days after UV irradiation, the UV-dependent keratinocyte thickening otherwise formed in the subsequent 5 days was suppressed.

The present invention provides a pharmaceutical composition comprising an IL-18 receptor antagonist, more specifically a pharmaceutical composition for preventing and/or treating an IL-18-related disorder, particularly for preventing and/or treating skin thickening, which comprises an antibody against the IL-18 receptor α subunit and/or an antibody against the β subunit. Furthermore, the present invention provides a method of inhibiting the growth of keratinocytes in the human skin, and a method of increasing the differentiation of keratinocytes. As used herein, the term "IL-18-related disorder" is intended to mean a disease, disorder, or illness that develops with the involvement of an IL-18-dependent intracellular signal transduction mechanism. Therefore, an "IL-18-related disorder" is characterized by the presence of activated form IL-18.

An IL-18 receptor antagonist according to the present invention has actions to suppress epidermal cell DNA synthesis, promote differentiation induction, and suppress epidermal thickening. Accordingly, an IL-18 receptor antagonist according to the present invention has an action to normalize the abnormal keratinization of skin epidermal cells, and can be used as a keratinization ameliorating agent. The keratinization ameliorating agent can be administered by internal, external application and any other methods; also, as active ingredients, in addition to an IL-18 receptor antagonist according to the present invention, anti-inflammatory agents, vitamins and the like in common use can be formulated as appropriate where necessary.

(a) Dermatological External Preparation

As used herein, the term "skin" is intended to mean the skin of the face, neck, chest, back, arm, leg, hand and scalp.

In one mode of embodiment, a pharmaceutical composition according to the present invention can be a dermatological external preparation comprising an IL-18 receptor antagonist according to the present invention. The dermatological external preparation can have various forms of use such as a medicinal dermatological external preparation, cosmetic medicinal dermatological external preparation, and cosmetic composition. As used herein, the term "dermatological external preparation" is intended to mean a medicinal dermatological external preparation or cosmetic medicinal dermatological external preparation; cosmetic compositions are described in detail below.

As the dermatological external preparation, a solid, semisolid or liquid preparation for transdermal administration, or suppositories and the like can be mentioned. For example, the dermatological external preparation can also be used as emulsified liquids such as emulsions and lotions, liquid preparations such as external tinctures, ointments such as oily ointment and hydrophilic ointment, and patches for transdermal administration such as films, tapes and cataplasms, and the like.

As examples of the medicinal dermatological external preparation and cosmetic medicinal dermatological external preparation, various ointments comprising a pharmacologically effective ingredient can be mentioned. The ointments may be any ones based on an oily base or based on an emulsion type base such as oil/water emulsion or water/oil emulsion. The above-described oily base is not subject to limitation; for example, vegetable oils, animal oils, synthetic oils, fatty acids, and natural or synthetic glycerides and the like can be mentioned. Also, the above-described pharmacologically effective ingredient is not subject to limitation; for example, anti-inflammatory analgesics, analgesics, bactericidal disinfectants, astringents, emollients, hormone preparations, vitamins and the like can be used as appropriate where necessary.

The dermatological external preparation according to this mode of embodiment can be produced by a method known in the field of pharmaceuticals. The content of IL-18 receptor antagonist in the dermatological external preparation according to this mode of embodiment is not subject to limitation, as long as it is an amount enabling the administration of the IL-18 receptor antagonist in the desired dose range, using the dermatological external preparation in consideration of the administration form, administration method and the like.

Although the amount of IL-18 receptor antagonist formulated in the dermatological external preparation according to this mode of embodiment is not subject to limitation, it is usually preferably 0.0001 to 5% by weight (hereinafter shown by "%"), particularly 0.0001 to 0.1%, to the total composition content, in the case of an emulsion type or oily dermatological external preparation.

An IL-18 receptor antagonist according to the present invention has a remarkable suppressive action on epidermal thickening and the like due to the influences of ultraviolet and other various factors, and, in addition, restores the normal function of the skin and allows the skin to maintain homeostasis. Therefore, using the dermatological external preparation according to this mode of embodiment, keratinization in portions of the skin that are likely to keratinize can be suppressed.

(b) Cosmetic Composition

In another mode of embodiment, a pharmaceutical composition according to the present invention can be a cosmetic composition. The cosmetic composition according to this mode of embodiment may occur in any form in common use in cosmetic products.

The cosmetic composition according to this mode of embodiment can be formulated with oils, moisturizers, ultraviolet absorber, whitening agents, alcohols, chelating agents, pH adjuster, antiseptics, thickeners, pigments, plant extracts, flavoring agents and the like in general use as cosmetic ingredients, in optionally chosen combinations. The cosmetic composition can be used in a variety of uses and forms, for example, water/oil or oil/water type emulsified cosmetics, creams, cosmetic emulsion, lotion, oily cosmetics, lipstics, foundations, skin cleansers, hair tonics, hair stylings, pilatory, hair restorer, and bath agents. The cosmetic composition according to this mode of embodiment can be prepared as the above-described variety of forms by a conventional method.

The cosmetic composition according to this mode of embodiment, as required, can occur in the form of a gelled aqueous solution, a lotion type dispersion, a double-phase lotion, an emulsion obtained by dispersing a oil phase in an aqueous phase (O/W emulsion), or a reverse emulsion (W/O emulsion), or a triple emulsion (W/O/W or O/W/o emulsion), or a vesicle dispersion of the ionic and/or non-ionic type.

The cosmetic composition according to this mode of embodiment may be a fluid or solid. When the cosmetic composition is provided as a fluid, it may have an appearance of white or colored cream, ointment, emulsion, lotion, essence, paste, or mousse. Furthermore, the cosmetic composition according to this mode of embodiment may be applied in the form of aerosol. The cosmetic composition according to this mode of embodiment can also be provided in a solid form, particularly in the form of a stick.

The cosmetic composition according to this mode of embodiment preferably comprises a pharmaceutically, particularly cosmetically, acceptable excipient that functions as a diluent, dispersing agent, or carrier, for the purpose of assisting the function of the IL-18 receptor antagonist (preferably anti-IL-18 receptor antibody) in the composition.

The excipient other than water, or added to water, can be a liquid or solid emollient, solvent, wetting agent, thickener, and powder.

In one mode of embodiment, a cosmetically acceptable excipient that can be used in the cosmetic composition according to this mode of embodiment generally constitutes 5% to 99.9%, preferably 25% to 80%, of the weight of the composition, and, in the absence of other cosmetic auxiliaries, constitutes the remaining portion of the composition. Preferably, at least 80% by weight of the weight of the excipient is water. Preferably, water constitutes at least 50% by weight, most preferably 60 to 80% by weight, of the novel composition.

In a preferred aspect, the cosmetic composition according to this mode of embodiment can contain an adjuvant in general use in cosmetic products (for example, hydrophilic or oleophilic gelling agents, hydrophilic or oleophilic activators, antiseptics, antioxidants, solvents, flavoring agents, fillers, screen agents, pigments, deodorants, dyes and the like). The amount of these various adjuvants is an amount in common use in the relevant field, and is, for example, 0.01% to 80%, preferably 0.01 to 50%, more preferably 0.05 to 30%, to the total weight of the composition. These adjuvants can be introduced to a fat phase, to an aqueous phase, or to a liquid vesicle, depending on the properties thereof. In all cases, a kind and ratio of the above-described adjuvant can be chosen in a way that does not damage the desired characteristics of the cosmetic composition according to this mode of embodiment.

Provided that the cosmetic composition according to this mode of embodiment is an emulsion, the ratio of fat phase can be in the range of 5 to 80% by weight, preferably 5 to 50% by weight, to the total weight of the composition. The oil, emulsifier, and co-emulsifier used in the composition in the form of emulsion are selected from among known substances in conventional use in the relevant field. The cosmetic composition according to this mode of embodiment can contain an emulsifier and co-emulsifier at a ratio in the range of 0.3 to 30% by weight, preferably 0.5 to 20% by weight, to the total weight of the composition.

As the oil that can be used in the cosmetic composition according to this mode of embodiment, mineral oils (liquid petrolatum or polyisobutene hydride), oils of plant origin (avocado oil or soybean oil), oils of mineral origin (lanolin), silicone oils (cyclomethicone or dimethicone), and fluoro oils (perfluoropolyethers) can be mentioned, but are not limited thereto. A fatty alcohol (cetyl alcohol), fatty acids, and waxes (carnauba wax or ozokerite) can also be used as the fatty substance.

As examples of the emulsifier and co-emulsifier that can be used in the cosmetic composition according to this mode of embodiment, fatty acid esters of polyethyleneglycol, for example, PEG-100 stearate, and fatty acid esters of glycerol, for example, glyceryl stearate, can be mentioned.

As the hydrophilic gelling agent that can be used in cosmetic composition according to this mode of embodiment, carboxyvinyl polymers (carbomers), acrylic acid polymers, for example, acrylate/alkylacrylate copolymer, polyacrylamides, particularly crosslinked polyacrylamide-methylpropane-sulfonic acid, polysaccharides, natural rubber and clay can be mentioned, but are not limited thereto. As the oleophilic gelling agent, denatured clays, for example, bentonite, metal salts of fatty acid, hydrophobic silica, and polyethylene can be mentioned.

The cosmetic composition according to this mode of embodiment preferably contains a sunscreen. "Sunscreen" is intended to mean a substance generally used to block ultraviolet. As examples of such compounds, derivatives of PABA, cinnamates, and salicylates can be used. As examples of the sunscreen, octylmethoxy cinnamate and 2-hydroxy-4-methoxybenzophenone (also known as oxybenzone) can be used. The exact amount of sunscreen in an emulsion can be varied depending on the desired degree of protection against solar ultraviolet.

An emollient can be contained in the cosmetic composition according to this mode of embodiment. The level of such emollient is 0.5% to 50%, preferably 5% to 30%, of the total weight of the composition. Emollients, in terms of general chemical species, can be classified as esters, fatty acids and alcohols, polyols and hydrocarbons.

The above-described esters can be mono- or di-esters. As examples of acceptable fatty acid diesters, dibutyl adipate, diethyl cebacate, diisopropyl dimelate, and dioctyl succinate can be mentioned. As acceptable branched fatty acid esters, 2-ethyl-hexyl myristate, isopropyl stearate, and isostearyl palmitate can be mentioned. As acceptable tribasic acid esters, triisopropyl trilinoleate and trilauryl citrate can be mentioned. As acceptable linear fatty acid esters, lauryl palmitate, myristyl lactate, and stearyl oleate can be mentioned. As preferable esters, coco-caprylate/caprate (a blend of coco-caprylate and coco-caprate), propylene glycol myristylether acetate, diisopropyl adipate, and cetyl octanoate can be mentioned.

As suitable fatty alcohols and acids, compounds having 10 to 20 carbon atoms can be mentioned. Compounds like cetyl, myristyl, palmitine, and stearyl alcohols and acids are particularly preferable.

The polyol that functions as an emollient can be a linear and branched alkylpolyhydroxyl compound (for example, propylene glycol, sorbitol, and glycerin are preferable; a polymer polyol like polypropylene glycol and polyethylene glycol). Butylene glycol and propylene glycol are also particularly preferable as penetration accelerators.

The hydrocarbon that functions as an emollient can be a hydrocarbon having a hydrocarbon chain having 12 to 30 carbon atoms. As preferable examples, mineral oil, petroleum jelly, squalene, and isoparaffin can be mentioned.

The cosmetic composition according to this mode of embodiment can contain a powder. As the powder, chalk, talc, kaolin, starch, smectite clay, chemically modified magnesium aluminum silicate, organically modified montmorillonite clay, hydrated aluminum silicate, fumed silica, aluminum starch octenyl-succinate, and mixtures thereof can be mentioned.

Other auxiliary minor ingredients can also be contained in the cosmetic composition according to this mode of embodiment. As these ingredients, coloring agents, opacifiers, and flavoring agents can be mentioned. The amount of these other auxiliary minor ingredients can be 0.001 to 20% by weight to the composition.

The cosmetic composition according to this mode of embodiment is intended to be used as a product for topical application to the human skin, particularly as a drug that conditions, moistens and smoothes the skin and prevents or reduces the appearance of streaked skin, wrinkled skin, or aged skin.

In using the cosmetic composition according to this mode of embodiment, a small amount, for example, 1 to 100 ml, of the composition is applied to an exposed surface of the skin from a suitable container or applicator, and, as required, spread and rubbed over the skin using a hand or finger or a suitable device.

In one mode of embodiment, a pharmaceutical composition for topical skin treatment according to the present invention can be prepared as a lotion, cream, or gel. The pharmaceutical composition according to this mode of embodiment can be packed in a container suitable for the viscosity and intended use thereof. The pharmaceutical composition according to this mode of embodiment, in the form of, for example, a lotion or cream, can be packed in a bottle or roll-ball applicator, or a container which has a propellant-driven aerosol device or a pump suitable for operation with a finger. In the form of a cream, the pharmaceutical composition according to this mode of embodiment may be housed in an undeformable bottle or squeeze container, for example, a tube or a wide-mouthed bottle with a lid, or sealed in a capsule. The pharmaceutical composition according to this mode of embodiment can be provided in a form housed in a tight container containing a cosmetically acceptable composition.

When compounded on a commercial base, the cosmetic composition according to this mode of embodiment can comprise various conventional colorants, flavoring agents, thickeners (xanthane gum and the like), antiseptics, wetting agents, emollients, palliatives, surfactants, dispersing agents, penetration accelerators and the like, and these can be added to obtain further advantages, and to improve the touch and/or appearance of the topical preparation. Likewise, this composition can be compounded in creams, lotions, ointments, soaps or liquid soaps, shampoos, masks and the like.

(c) Drug Composition

In still another mode of embodiment, a pharmaceutical composition according to the present invention can be a drug composition. A drug carrier used in the drug composition can be chosen according to the administration form and dosage form of the drug composition. As used herein, the term "drug composition" is intended to mean a composition having a form other than the above-described pharmaceutical compositions provided as dermatological external preparation and cosmetic composition.

In the case of an oral formulation, for example, starch, lactose, sucrose, mannitol, carboxymethylcellulose, cornstarch, inorganic salts and the like are utilized as drug carriers. Also, in preparing an oral formulation, a binder, disintegrant, surfactant, lubricant, fluidity promoter, taste corrective, coloring agent, flavoring agent and the like may further be formulated.

In the case of a non-oral formulation, it can be prepared by dissolving or suspending the active ingredient of the present invention in distilled water for injection, physiological saline, aqueous glucose solution, vegetable oil for injection, sesame oil, peanut oil, soybean oil, corn oil, propylene glycol, polyethylene glycol and the like as a diluent according to a known method in the relevant field, and as desired adding a bactericide, stabilizer, isotonizing agent, soothing agent and the like.

The drug composition according to this mode of embodiment can be produced by a known method in the field of pharmaceutical making. The content of IL-18 receptor antagonist in the drug composition according to this mode of embodiment is not subject to limitation, as long as it is an amount enabling the administration of the IL-18 receptor antagonist in the dose range described below, using the drug composition in consideration of the administration form, administration method and the like.

The drug composition according to this mode of embodiment can be administered via an appropriate route of administration according to the preparation form. The administration method is also not subject to limitation, and can be by internal, external application and injection. Because the drug composition according to this mode of embodiment can be used as an ameliorating agent or prophylactic agent for skin thickening, it is applicable as an ameliorating agent or prophylactic agent for wrinkles, an agent for improving or maintaining skin elasticity, or a collagen production enhancer or reduction suppressant; when the drug composition according to this mode of embodiment is used for these uses, it is particularly suitable to administer the drug composition by application to the skin as the above-described dermatological external preparation, whereby a desired effect can be obtained. The injection can be administered, for example, intravenously, intramuscularly, subcutaneously, intradermally and the like.

The dose of the drug composition according to this mode of embodiment is established as appropriate according to the preparation form, administration method, and intended use thereof and the age, body weight, and symptoms of the patient to receive the drug, and is not constant. Generally, the dose of the active ingredient contained in the preparation is preferably 0.1 to 2000 mg/kg per day for an adult. Of course, because the dose varies depending on various conditions, a dose smaller than the above-described dose is sufficient in some cases, and a dose beyond the range is necessary in other cases. Administration may be performed at a time or in several divided portions in a day within the desired dose range. Also, the drug composition according to this mode of embodiment may be administered orally as is, and may also be routinely taken as an additive to an optionally chosen drink or food.

Using the drug composition according to this mode of embodiment, the overgrowth of keratinocytes accompanying UV-induced dermatitis, skin hyperplasia after burns, contact dermatitis and the like can be prevented.

(d) Food Composition

In another mode of embodiment, the present invention provides a food composition (that is, a food, beverage, or feed) for ameliorating or preventing skin thickening, which has an IL-18 receptor antagonist contained therein, added thereto and/or diluted therein. The food composition according to this mode of embodiment is extremely useful in ameliorating or preventing symptoms that accompany skin thickening in individuals showing sensitivity to the IL-18 receptor antagonist by the physiological action of the IL-18 receptor antagonist.

In this mode of embodiment, "contain" refers to the mode wherein an IL-18 receptor antagonist is contained in a food composition (that is, a food, beverage, or feed), "add" refers to the mode wherein an IL-18 receptor antagonist is added to the raw material for a food composition, and "dilute" refers to the mode wherein an IL-18 receptor antagonist is diluted with the raw material of a food composition. Also, the term "contain" as used in the statements about the above-described cosmetic composition according to the present invention includes the meanings of "contain", "add", and "dilute" as mentioned in the mode of the present invention.

The production method for the food composition according to this mode of embodiment is not subject to limitation; cooking, processing and production by a food or beverage production method in general use can be mentioned, as long as the food or beverage produced has an IL-18 receptor antagonist according to the present invention contained therein, added thereto and/or diluted therein.

The food composition according to this mode of embodiment is not subject to limitation; for example, processed cereal products (processed flour products, processed starch products, processed premix products, noodles, macaronis, breads, bean jams, soba (buckwheat noodles), fu (dried bread-like pieces of wheat gluten), rice noodles, harusame (bean-starch vermicelli), packed rice cakes and the like), processed oil and fat products (plastic oils and fats, tempura oil (deep-fried oil), salad oil, mayonnaises, dressings and the like), processed soybean products (tofu (soybean curd), miso (soybean paste), natto (fermented soybean) and the like), processed meat products (hams, bacons, pressed hams, sausages and the like), marine products (frozen surimi (frozen minced fish), kamaboko (steamed fish paste), chikuwa (a kind of fish paste), hanppen (fish minced and steamed), satsumaage (fried fish balls), tsumire (minced fish), sinew, fish hams, fish sausages, kastuobushi (dried bonito), processed fish egg products, canned marine products, tsukudani (fish boiled in soysauce) and the like), dairy products (raw material milk, cream, yogurt, butter, cheese, condensed milk, powdered milk, ice cream and the like), processed vegetable/fruit products (pastes, jams, pickles, fruit beverages, vegetable beverages, mixed beverages and the like), sweets (chocolate, biscuits, sweet buns, cakes, rice cake confectionery, rice crackers and the like), alcoholic beverages (Japanese sake, Chinese spirits, wine, whisky, shochu spirits, vodka, brandy, gin, rum, beer, refreshing alcoholic beverages, fruit spirits, liqueur and the like), table luxury beverages (green tea, black tea, oolong tea, coffee, refreshing beverages, lactic acid beverages and the like), seasonings (soysauces, sauces, vinegar, sweet sake and the like), canned/bottled/pouched foods (beef rice, kamameshi (boiled rice with assorted mixtures in earthen pot), sekihan (festival red rice), curry, and other various cooked foods), semi-dry or concentrated foods (liver paste, other spreads, soba (buckwheat noodles)/udon (wheat noodles) stocks, concentrated soups), dry foods (instant noodles, instant curry, instant coffee, powdered juices, powdered soups, instant miso soup, cooked foods, cooked beverages, cooked soups and the like), frozen foods (sukiyaki, chawanmushi (pot-steamed hotchpotches), broiled eels, hamburger steak, shao-mai, gyoza (steam-baked meat pie), various sticks, fruit cocktails and the like), solid foods, liquid foods (soups and the like), processed agricultural and forestry products such as spices, processed livestock products, and processed marine products can be mentioned.

The content of an IL-18 receptor antagonist according to the present invention in the food composition according to this mode of embodiment is not subject to limitation, and can be chosen as appropriate from the viewpoint of its sense and action onset; for example, the content is preferably 0.0001 part by weight or more, more preferably 0.001 to 10 parts by weight, per 100 parts by weight of a food, and is preferably, for example, 0.0001 part by weight or more, more preferably 0.001 to 10 parts by weight, per 100 parts by weight of a beverage.

The production method for the food composition according to this mode of embodiment is not subject to limitation, and the food composition can be produced in accordance with an ordinary food production method, as long as an effective amount of IL-18 receptor antagonist is contained in, added to, and/or diluted in the feed produced.

A food, beverage or feed according to the present invention is not subject to limitation as to the shape thereof, as long as it has an IL-18 receptor antagonist according to the present invention contained therein, added thereto, and/or diluted therein, in an effective amount to allow the physiological action thereof to be exhibited, and it includes orally ingestible forms such as tablets, granules, and capsules. Note that an IL-18 receptor antagonist according to the present invention is extremely useful as a raw material for the production of a food, beverage or feed as a healthful food material having both the physiological action and dietary fiber function.

Furthermore, in another mode of embodiment, use of an IL-18 receptor antagonist according to the present invention to produce a drug for ameliorating or preventing skin thickening is provided.

Note that when an IL-18 receptor antagonist according to the present invention is administered singly at 5 g/kg body weight in intraperitoneal administration to rats, no deaths are observed. Also, no adverse drug reactions are observed.

(e) External Preparation for Hair Growth and Hair Restoration

In still another mode of embodiment, a pharmaceutical composition according to the present invention can be an external preparation for hair growth and hair restoration. After shaving, at the irradiation site of keratinocytes of a UV-irradiated wild type mouse, hair re-growth is observed after 12 days following the irradiation. However, when an IL-18 receptor antagonist was applied or intraperitoneally administered, hair re-growth was observed 7 days after the irradiation.

The external preparation for hair growth and hair restoration according to this mode of embodiment can be prepared as a conventionally known dosage form of external preparation. Particularly preferably, the external preparation for hair growth and hair restoration is prepared in a dosage form such as dermatological pastes, ointments, creams, solutions, gels, triturations, powders, and bath agents. Also, the external preparation for hair growth and hair restoration can be used in a mode utilizing the above-described dosage forms, for example, shampoo, rinse, conditioner, hair tonic, hair cream, hair liquid, hair milk, hair mist, hair foam, hair gel, hair spray and the like.

Preparation of the External Preparation for Hair growth and hair restoration according to this mode of embodiment can be performed by mixing and homogenizing IL-18 and an external preparation ingredient in common use in pharmaceutical making by a conventional method according to the above-described dosage forms.

As specific examples of the base ingredients out of the external preparation ingredients used in preparing the external preparation for hair growth and hair restoration according to this mode of embodiment, the following ingredients, for example, can be mentioned.

As examples of the fats, medium-chain fatty acid triglycerides, synthetic oils such as hard fats, vegetable oils such as olive oil, soybean oil, rapeseed oil, peanut oil, safflower oil, rice bran oil, sesame oil, camellia oil, corn oil, cottonseed oil, and coconut oil, animal oils such as lard and beef tallow, hardened oils thereof and the like can be mentioned; these may be used singly or in combination of two kinds or more.

As examples of the waxes, natural waxes such as lanolin, beeswax, carnauba wax, and whale wax, mineral waxes such as montan wax, synthetic waxes and the like can be used; as examples of the hydrocarbons, petrolatum (white petrolatum, yellow petrolatum), paraffin, liquid paraffin, microcrystalline wax, squalan, polyethylene powder, gelled hydrocarbons and the like can be used. These may be used singly or in combination of two kinds or more.

As examples of the higher fatty acids, stearic acid, behenic acid, palmitic acid, oleic acid and the like can be used. Also, as examples of the higher alcohols, cetanol, stearyl alcohol, oleyl alcohol, cholesterol and the like can be used; as examples of the polyvalent alcohols, propylene glycol, polyethylene glycol, glycerin, 1,3-butylene glycol and the like can be used. These may be used singly or in combination of two kinds or more.

As examples of the synthetic and natural polymers, carrageenan, starch, dextrin, dextrin polymer (cadexomer), tragacanth, gum arabic, locust bean gum, pectin, gelatin, xanthane gum, pullulan, alginate, hydroxypropylcellulose, carboxymethylcellulose sodium, polyacrylate, polyvinyl alcohol, polyvinylpyrrolidone, carboxyvinyl polymer and the like can be used. Also, as examples of the surfactants, alkyl sulfate, polyoxyethylene alkylether phosphate, glycerin fatty acid esters, polyglycerin fatty acid esters, sorbitan fatty acid esters, polyoxyethylene sorbitan fatty acid esters, polyoxyethylene hardened castor oil, polyethylene glycol fatty acid esters, polyoxyethylene polyoxypropylene glycol, polyoxyethylene alkylethers, sucrose fatty acid esters and the like can be used. Also, these may be used singly or in combination of two kinds or more.

As examples of the lower alcohols, ethanol, isopropyl alcohol and the like can be used. As examples of the ketones, acetone, methyl ethyl ketone and the like can be used. As examples of the powders, kaolin, talc, zinc oxide, titanium oxide, magnesium stearate, silicic anhydride, starch and the like can be used. As examples of the cellulose derivatives, methylcellulose, carboxymethylcellulose sodium, hydroxypropylcellulose and the like can be used. As examples of the inorganic salts, sodium sulfate, sodium hydrogen carbonate, sodium chloride, calcium nitrate, potassium nitrate, sodium nitrate, aluminum sulfate, sodium polyphosphate, ammonium chloride, iron sulfate, sodium phosphate, magnesium sulfate, sodium thiosulfate, sodium sesquicarbonate, sodium sulfide, borax, calcium oxide, magnesium carbonate, potassium chloride and the like can be used. Also, these may be used singly or in combination of two kinds or more.

More specifically, the relationship between each dosage form and additive ingredients is described below.

Dermatological pastes can be used in the dosage form of oily dermatological pastes or aqueous dermatological pastes; in the case of oily dermatological pastes, as the base ingredient, for example, fats, waxes, hydrocarbons and the like can be used. Also, in the case of aqueous dermatological pastes, as the base ingredient, for example, synthetic and natural polymers, polyvalent alcohols, surfactants and the like can be used.

In the case of ointments, as the base ingredient, for example, fats, polyvalent alcohols, hydrocarbons and the like can be used.

In the case of creams, as the base ingredient, for example, surfactants, higher alcohols, higher fatty acids, hydrocarbons, polyvalent alcohols, water (including purified water) and the like can be used.

In the case of solutions and gels, as the base ingredient, for example, water (including purified water), lower alcohols, ketones, fats, polyvalent alcohols, surfactants, hydrocarbons, synthetic and natural polymers and the like can be used.

In the case of triturations and powders, as the base ingredient, for example, powder ingredients, cellulose derivatives, synthetic and natural polymers and the like can be used.

In the case of bath agents, a phosphenolpyruvate ingredient which is an active ingredient may be used alone, and, as further constituent ingredients, inorganic salts and the like can be used in a formulation.

In the external preparation for hair growth and hair restoration according to this mode of embodiment, as required, for example, alkali metal hydroxides such as sodium hydroxide and the like can be used as pH adjuster, and, as antiseptics/preservatives, for example, alkali metal salts of benzoic acid such as sodium benzoate, p-hydroxybenzoate ester, sorbic acid and the like may be formulated. Furthermore, also as required, as antioxidants, for example, tocopherol, dibutylhydroxytoluene, butylhydroxyanisole and the like may be used.

Also, the external preparation for hair growth and hair restoration according to this mode of embodiment may be further formulated with other compounds expected to have a hair restoration promoting effect in order to enhance the effect on hair growth and hair restoration as required. As examples of such compounds, vitamins (vitamin As such as retinol, retinal, and retinoic acid, vitamin A esters such as retinol fatty acid esters, retinol acetate, retinol palmitate, α-carotene, β-carotene, γ-carotene, lycopene, thiamine nitrate, thiamine hydrochloride, thiamine disulfide compounds, riboflavin, flavin nucleotide, flavin tetrabutyrate, riboflavin tetranicotinate, pyridoxine hydrochloride, pyridoxal hydrochloride, pyridoxamine hydrochloride, cyanocobalamine, nicotinic acid, nicotinic amide, methyl nicotinate, benzyl nicotinate, pantothenic acid, pantothenates, pantothenyl alcohol, pantothenyl ethyl ether, biotin, ascorbic acid, ascorbate, ascorbic acid esters, vitamin Ds, tocopherol, tocopherol acetate, ubiquinone, plastoquinone, vitamin Ks and the like), choline, essential fatty acids (linoleic acid, linolenic acid, arachidonic acid), eicosatrienoic acid, female hormone, adrenocortical hormone, antihypertensives (minoxidil, diazoxide and the like), TCA cycle-related substances (c-AMP, succinic acid, citric acid, ATP, FAD, NAD, NADP, L-malic acid, methylmalonyl CoA, fumaric acid, succinyl CoA, coenzyme A, GDP, GTP, ADP, AMP, oxaloacetic acid, acetyl CoA and the like), plant extracts (hinokithiol, clove extract, aloe extract, licorice extract, zanthoxylum extract, Rehmannia glutinosa var. purpurea extract, *swertia* herb extract liquid, hop extract liquid, rosemary extract liquid, sage extract liquid, thyme extract liquid, genseng extract liquid, garlic extract liquid and the like) and synthetic pharmacologically effective ingredients (capronium chloride and the like) and the like can be mentioned; these may be used singly or in combination of two kinds or more.

The external preparation for hair growth and hair restoration according to this mode of embodiment can be prepared as an emulsion-type preparation; in this case, the form of the emulsion may be any of the W/O type, O/W type, W/O/W type, and O/W/O type.

Also, although the external preparation for hair growth and hair restoration according to this mode of embodiment per se may be applied as is to an affected area, this external preparation may also be applied to the affected area as, for example, patches such as what are called cataplasms and plasters, applied to an elastic cloth, unwoven fabric or plastic sheet and the like.

The external preparation for hair growth and hair restoration according to this mode of embodiment is safe to the skin, offers a good feeling of use, is clinically excellent, and is capable of having an excellent action on hair growth and hair restoration. Therefore, the external preparation for hair growth and hair restoration of the present invention is capable of having a sufficient effect in the promotion of hair growth and hair restoration, prevention of thin hair/alopecia (hair loss), or treatment of androgenetic alopecia, convalescent/postpartum alopecia, alopecia greata, hair growth insufficiency, alopecia pityrodes, seborrheic alopecia, diffuse alopecia, young baldness (common baldness) and elderly baldness (alopecia senilis) and the like.

Hence, it can be said that a pharmaceutical composition according to the present invention may be any one comprising at least an IL-18 receptor antagonist according to the present invention. Therefore, it should be noted that pharmaceutical compositions comprising another ingredient are also included in the technical scope of the present invention.

(f) Involvement of IL-18 in Stress-Related Disease

It has been shown to date that the nervous system, the endocrine system and the immune system interact with each other to constitute a major host defense network. It has been proposed that controlling these interactions could be an important therapeutic strategy for autoimmune disease and inflammatory disease.

The present inventors found, as described above, that by UV irradiation, that is, oxidative stress, the expression of IL-18 was facilitated at the irradiation site, and that by an IL-18 receptor antagonist, disorders caused by the oxidative stress were suppressed. This suggests that the expression of IL-18 may increase in response to various stresses, not limited to UV irradiation, and stress-related disease may occur as a result of the expression of IL-18.

Accordingly, the present inventors examined how IL-18 is involved in various stress loads. As a result, the present inventors found that IL-18 was involved in the interactions among the nervous system, the endocrine system and the immune system. Specifically, the present inventors found that a large amount of activated form IL-18 (18-kD protein) was secreted in the plasma of mice exposed to immobilization stress.

As used herein, the term "stress-related disease" is intended to mean a disease or disorder resulting from a non-infectious, non-chemical or non-injurious invasion from the outer world, and a response of an individual thereto (that is, stress), specifically a disease that can occur, exacerbate and/or progress due to physical, physiological, psychological, mental, or age-related invasion, and a disease the risk of onset thereof increases due to these invasions.

As the disease suggested to be associated with stress, psychosomatic disorder, appendicitis, peptic ulcers, gastric ulcer, duodenal ulcer, peritonitis, pancreatitis, ulcerative, pseudomembranous, acute and ischemic colitis, diverticulitis, epiglottitis, achalasia, cholangitis, cholecystitis, hepatitis, Crohn's disease, enterocolitis, Whipple's disease, asthma, allergies, anaphylactic shock, immune complex disease, ischemia of organs, repurfusion injury, necrosis of organs, hay fever, sepsis, septicemia, endotoxin shock, cachexia, hyperpyrexia, eosinophilic granuloma, granulomatous, sarcoidosis, septic abortion, epididymitis, vaginitis, prostatitis, urethritis, bronchitis, pulmonary emphysema, rhinitis, cystic fibrosis, pneumonia, pneumoconiosis, alveolitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, dengue fever, candidiasis, malaria, filariasis, amebiasis, hydatid cysts, burns, dermatitis, dermatomyositis, sunburns, urticaria, warts, wheals, angiitis, vasculitis, endocarditis, arteritis, atherosclerosis, thrombophlebitis, pericarditis, myocarditis, myocardial ischemia, periarteritis nodosa, rheumatic fever, Alzheimer's disease, celiac disease, congestive heart failure, adult respiration distress syndrome, meningitis, encephalitis, multiple sclerosis, cerebral infarction, cerebral apoplexy, Guillain-Barre syndrome, neuritis, neuralgia, spinal injury, paralysis, uveitis, arthritic eruption, arthralgia, osteomyelitis, fasciitis, Paget's disease, gout, periodontal disease, rheumatoid arthritis (RA), synovitis, myasthenia gravis, amyotrophic lateral sclerosis, thyroiditis, systemic lupus erythematosus, Goodpasture's syndrome, Behçet's syndrome, graft rejection in allotransplantation, graft-versus-host disease, type I diabetes mellitus, ankylosing spondylitis, Buerger's disease, type II diabetes mellitus, ankylosing spondylitis, Buerger's disease, Reiter's syndrome, Hodgkin's disease, SLE, liver cirrhosis, renal insufficiency, allergic asthma, nephritis, myocardial infarction, Sjoegren's syndrome, contact-type dermatitis, atopic dermatitis, depression, eating disorders, allotriophagy, dysgeusia, acne vulgaris, pemphigus, ichthyosis, psoriasis, burns, photosensitivity, ultraviolet dermopathy, or radiation disorders, carbon monoxide poisoning, hypoxia or deuteropathy thereto and the like can be mentioned.

In these stress-related diseases, particularly in rheumatic arthritis, systemic lupus erythematosus, multiple sclerosis, acne vulgaris, Crohn's disease, ulcerative colitis, atopic dermatitis, bronchial asthma, Sjoegren's syndrome, depression, and psychosomatic disease, it has been suggested that IL-6, which is a kind of cytokine, may be involved. In these diseases, the IL-6 concentration in serum rises according to the stress. Particularly in rheumatic arthritis, systemic lupus erythematosus, and multiple sclerosis, it has been reported that the illness is ameliorated by using an anti-IL-6 receptor antibody in experiments using respective animal models. However, when an anti-IL-6 receptor antibody is applied to a human (patient), the effect does not persist and a drawback of inconsistent effect occurs.

The elevation of the concentration of blood IL-18 released due to stress originates from the adrenal. In patients with the above-described stress-related disease, it has been reported that irrespective of stress, IL-18 has risen (rarely decreased in atopic dermatitis). It has been shown that the promoter site for activation of IL-18 production differs between the elevation of IL-18 released due to stress and the elevation of IL-18 released due to inflammation or infection; therefore, it has been totally unknown whether or not the elevation of IL-18 observed in stress-related disease is due to stress.

(g) Effects of IL-18 Receptor Antagonists on Stress-Related Disease

The present inventors found that if further stress was exerted on animal models (wild type, model mouse of collagen-induced rheumatoid arthritis or systemic lupus erythematosus), a significant elevation of IL-18 in plasma was observed within several hours, and that this elevation was suppressed by superoxide dismutase (SOD), an enzyme for elimination of active oxygen, a p38 MAPK inhibitor, a caspase-11 inhibitor, and a caspase-1 inhibitor. This shows that a particular pathway for upregulating IL-18 exists, and that irrespective of the severity of underlying inflammatory disease, this pathway is activated. Also, this result shows that unless ACTH secretion capability, adrenocortical function, and/or general protein synthesis capability is originally disordered, the blood IL-18 concentration rises due to stress in all diseases.

In model mouse of multiple sclerosis, Sjoegren's syndrome, rheumatoid arthritis (RA) or systemic lupus erythematosus (SLE), elevations of blood IL-18 concentration and subsequent elevations of blood IL-6 concentration were observed before the symptoms and signs exacerbated. Particularly, when model mouse of collagen-induced rheumatoid arthritis or systemic lupus erythematosus were loaded with 3 hours of stress every two-days, the completion of the pathology was speeded and the symptoms and signs exacerbated. Also, in a group receiving IL-18 receptor antagonists (anti-α antibody+anti-β antibody) intraperitoneally at 25 µg/kg (12.5 µg of each antibody) immediately before stress (10 minutes before), amelioration of exercise and/or gait in RA, and significant amelioration of lupus nephritis (BUN and urinary albumin) in SLE were observed, and stress-related exacerbation was avoided. Although the same result was observed also when a commercially available anti-IL-6 antibody (Santa Cruz 1265) and anti-IL-6 receptor antibody (Santa Cruz 660) were used, the IL-18 receptor antagonists were more effective than the anti-IL-6 antibody or anti-IL-6 receptor antibody.

Also, in experiments using wild type mouse and a model mouse of systemic lupus erythematosus, a suppression of the elevation of blood IL-6 concentration was observed when IL-18 receptor antagonists (anti-α antibody+anti-β antibody) were administered 30 minutes after the start of stress.

From the results above, it was shown that in stress-related disease, a stress-induced elevation of blood IL-18 concentration and a subsequent elevation of blood IL-6 concentration occurred and the symptoms and signs exacerbated, that using an IL-18 receptor antagonist (particularly an anti-receptor antibody), the blood concentration not only of IL-18, but also of IL-6, could be suppressed, and that using an IL-18 or IL-6 receptor antagonist, it was possible to suppress the blood concentrations thereof, and as a result to suppress the exacerbation of symptoms and signs.

Blood IL-18 has a very longer half-life than that of blood IL-6. Therefore, targeting IL-18 in the treatment of stress-related disease (that is, treating using an anti-IL-18 receptor antibody) is more effective than treating stress-related disease using an anti-IL-6 antibody or anti-IL-6 receptor antibody. This agrees with the fact that anti-IL-18 receptor antibodies (anti-α antibody+anti-β antibody) were more effective than anti-IL-6 antibody or anti-IL-6 receptor antibody in the treatment of stress-related disease.

As described above, an IL-18 receptor antagonist according to the present invention enables to treat stress-related disease. Therefore, the present invention also provides a pharmaceutical composition for treating a stress-related disease, which comprises an IL-18 receptor antagonist according to the present invention.

A pharmaceutical composition according to the present invention may be the above-described dermatological external preparation, cosmetic composition, or another drug composition. The dosage form and administration form of a pharmaceutical composition according to the present invention, and the carrier contained in the composition may be chosen as appropriate from among those described in the above-described sections for dermatological external preparation, cosmetic composition, or other drug composition.

As used herein, the term "IL-18/IL-6-related disorder" is intended to mean a disease, disorder, or illness characterized by an elevation of blood IL-18 level and elevation of blood IL-6 level, like a stress-related disease.

3: Pharmaceutical Composition Comprising IL-18

(a) Effects of IL-18 on Apoptosis

The present inventors found as a new function of IL-18 identified as an interferon γ inducing factor to suppress and/or inhibit apoptosis.

Usually, normal cultured cells undergo inhibition of the growth thereof due to cell contact prevention when subjected to mono-layer culture, but in cells with abnormal cell cycles like cancer cells, cell contact prevention does not occur and the cells continue to grow.

The present inventors found that when activated form IL-18 was added to the culture medium for keratinocytes cultured at high density, apoptosis due to cell contact prevention was suppressed. Furthermore, the present inventors found that when an anti-IL-18 antibody was added to the culture supernatant of differentiation-induced cultured keratinocytes, apoptosis occurring in the differentiation process was suppressed. Hence, the present inventors investigated to determine whether or not apoptosis could be controlled via an IL-18-related signal transduction pathway.

As the dermopathy after UV irradiation, inflammatory reactions in the acute stage, epidermal gene disorders, occurrence of skin thickening and desquamation due to overgrowth of keratinocytes, and suppression of tissue immunity can be mentioned. It was found that on the above-described disorders, IL-18 had the following effects:

in the acute stage, IL-18 prevented epithelial loss due to excess apoptosis;

in the middle and late stages, IL-18 caused overgrowth of keratinocytes and elicited immunosuppression in skin tissue (induction of IL-4 and IL-10).

From the results of experiments using cultured keratinocytes, IL-18 causes signal transduction via p38 MAPK and MEK3/6 to cells in the initial stage of differentiation induction. IL-18 exhibits functions as a survival factor, differentiation-inducing factor, and growth inducing factor in the respective stages of differentiation. On the other hand, by inhibiting IL-18 using an IL-18 receptor antagonist, skin hyperplasia or keloid formation was prevented.

Because a pharmaceutical composition comprising IL-18 according to the present invention acts to promote the keratinization of the skin, it has an ameliorating effect on skin pigmentation (whitening effectiveness) by accelerating the metabolism of melanin, which is the causal substance for skin pigmentation caused by sunburns and the like, and can be used as a whitening agent. The keratinization ameliorating agent and whitening agent can be administered by internal, external application and any other methods, and can be formulated as appropriate with anti-inflammatory agents, vitamins and the like in common use, in addition to IL-18, as active ingredients as required.

In one mode of embodiment, the present invention provides a composition having anti-apoptosis action, which comprises IL-18. As used herein, the term "anti-apoptosis action" is intended to mean that the number of apoptotic cells decreases, that is, apoptosis is suppressed and/or inhibited.

It can be said that a pharmaceutical composition according to the present invention may be any one comprising at least IL-18. Therefore, it should be noted that pharmaceutical compositions comprising other ingredients are also included in the technical scope of the present invention.

4: Pharmaceutical Composition for Preventing and/or Treating IL-18-Related Disorder As described above, the present inventors found that when further stress was exerted on animal models (wild type, model mouse of collagen-induced rheumatoid arthritis or systemic lupus erythematosus), a significant elevation of IL-18 in plasma was observed within several hours, and that this elevation was suppressed by superoxide dismutase (SOD), an enzyme for elimination of active oxygen, a p38 MAPK inhibitor, a caspase-11 inhibitor, and a caspase-1 inhibitor. Furthermore, by IL-18 receptor antagonists, the stress-dependent elevation of blood IL-18 concentration was suppressed. From these facts, it was found that superoxide dismutase (SOD), a p38 MAPK inhibitor, a caspase-11 inhibitor, or a caspase-1 inhibitor was effective in treating an IL-18-related disorder, preferably stress-related disease.

In one aspect, a pharmaceutical composition according to the present invention is characterized by comprising superoxide dismutase for preventing and/or treating an IL-18-related disorder.

In another aspect, a pharmaceutical composition according to the present invention is characterized by comprising a p38 MAPK inhibitor for preventing and/or treating an IL-18-related disorder.

In still another aspect, a pharmaceutical composition according to the present invention is characterized by comprising a caspase-1 inhibitor for preventing and/or treating an L-18-related disorder.

In still yet another aspect, a pharmaceutical composition according to the present invention is characterized by comprising a caspase-11 inhibitor for preventing and/or treating an IL-18-related disorder.

A pharmaceutical composition according to the present invention may be the above-described dermatological external preparation, cosmetic composition, or other drug composition. The dosage form and administration form of a pharmaceutical composition according to the present invention and the carrier contained in the composition may be chosen as appropriate from among those described in the above-described sections for dermatological external preparation, cosmetic composition, or other drug composition.

It can be said that a pharmaceutical composition according to the present invention may be any one comprising at least superoxide dismutase (SOD), a p38 MAPK inhibitor, a caspase-11 inhibitor, or a caspase-1 inhibitor. Therefore, it should be noted that pharmaceutical compositions comprising other ingredients are also included in the technical scope of the present invention.

The present invention is hereinafter described in more detail by means of the following Examples, but is not to be limited thereto.

EXAMPLES

Example 1

Generation of Anti-IL-18 Receptor Antibodies

According to an anti-peptide antibody experimental protocol (Shujunsha, 1994), antibodies against the IL-18 receptor α subunit and β subunit were produced. Specifically, peptides having the amino acid sequences shown by SEQ ID NO:5 to 10 were prepared (MBL Company), and these synthetic peptides were coupled with KLH (Calbiochem (374805)) using the MBS method, after which each coupled antigen (200 μg) was suspended in 1.5 ml of Freund's complete adjuvant (IATRON LABORATORIES) to prepare an antigen liquid, and a rabbit (Japanese White) were immunized with this antigen liquid by subcutaneous injection to the back thereof.

(Table 1: Peptide Antigens for Generating Anti-Receptor Antibodies)

TABLE 1

| Designation | Derivation | Amino acid positions | Sequence | SEQ ID NO |
|---|---|---|---|---|
| Peptide α-A | Human | 120-140 | FTERQVTSKIVEVKK FFQITC | 5 |
| Peptide α-B | Human | 142-162 | NSYYQTLVNSTSLYK NCKKLL | 6 |
| Peptide α-C | Mouse | 99-116 | SQVGNDRRNWTLNVT KRN | 7 |
| Peptide α-D | Mouse | 252-270 | DSSDPNVQEDRKETT TWIS | 8 |
| Peptide β-E | Human | 21-42 | NISGCSTKKLLWTYS TRSEEEF | 9 |
| Peptide β-F | Human | 164-190 | DLLLGSTGSISCPSL SCQSDAQSPAVT | 10 |

Subsequently, the above-described coupling antigen (200 μg) was suspended in 1.5 ml of Freund's incomplete adjuvant (IATRON LABORATORIES) to prepare an additional antigen liquid. One week after the first antigen liquid injection, this additional antigen liquid for booster immunization was subcutaneously injected 5 times at 1-week intervals. One week later, venous blood (20 ml or 100 ml) was drawn from the subaural vein using a 22-G indwelling needle. The venous blood drawn was allowed to stand at 37° C. for 1 hour, after which it was centrifuged at 3,000 rpm for 30 minutes (4° C.), and a serum fraction was extracted to obtain antisera containing the desired antibodies (anti-α antisera (A to D) and anti-β antisera (E and F)).

As required, using CNBr-activated Sepharose 4B (Pharmacia) columns coupled with respective antigen peptides, the antibodies were affinity-purified from the antisera.

Example 2

Investigation of Anti-IL-18 Receptor Antibodies

As anti-IL-18 receptor α subunit antibodies, ACRIS Company's MsAgG1 (H44 clone: anti-human) and GT Company's 70625 14-P398 (anti-human) and 112624 14-P398 (anti-human) are currently commercially available, whereas no anti-IL-18 receptor β subunit antibody is commercially available.

The anti-α antisera obtained in Example 1 (A to D) were compared with a commercially available anti-IL-18 receptor α subunit antibody.

The above-described commercially available anti-IL-18 receptor α subunit antibodies are used for flowcytometry in cultured KG-1 cell samples, Western blot and ELISA in cultured KG-1 cell samples, neutralization of the IFN-γ productivity of IL-18 secreted by cultured KG-1 cells, and the like, but cannot be used for immunohistochemistry of tissue specimens and Western blot of tissue extract.

Recombinant human IL-18 (40 ng/ml) was added to a culture medium for commercially available human keratinocyte KG-1 cells (Cambrex Company, USA) at $1 \times 10^5$ cells/plate. As the recombinant human IL-18, the recombinant protein described in J. Immunol. 156: 4274-9 (1996) and Nature 378: 88-91 (1995) was used.

Using a commercially available anti-IL-18 receptor α subunit antibody (ACRIS Company's MsAgG1) and the anti-α antisera obtained in Example 1 (A to D) at the same protein content, the neutralization of recombinant IL-18-dependent IFN-γ productivity in KG-1 cells was compared.

The neutralizing activities of all of the anti-α antisera obtained in Example 1 were nearly the same as the neutralizing activity of the commercially available α subunit antibody. These anti-α antisera (A to D) were found to have a neutralizing activity sufficiently more potent than that of the commercially available α subunit antibody because they contain antibodies other than α subunit antibodies. Also, all of the anti-β antisera obtained in Example 1 (E and F) had nearly the same levels of neutralizing activity as those of the anti-α antisera (A to D).

Next, using these anti-α antisera (A to D) and anti-β antisera (E and F), flowcytometry, immunoprecipitation, Western blot, ELISA (brain homogenate soluble fraction, cultured KG-1 cells, and mouse peritoneal macrophage), and immunohistochemistry (OCT frozen, fresh frozen, paraffin-embedded sections) were performed. Whatever the antiserum used, clear results were obtained in the above-described experiments.

Furthermore, antisera obtained by immunization using a mixed antigen of peptide α-A and peptide α-B, a mixed antigen of peptide α-C and peptide α-D, and a mixed antigen of peptide β-E and peptide β-F were further affinity-purified (anti-human α antibody, anti-mouse α antibody and anti-β antibody, respectively). Using these antibodies, as with the above-described antisera, clear results were obtained in the above-described experiments. Particularly, in Western blot analysis, the backgrounds were lower than those obtained using the above-described antisera; even when the protein content of the sample used in the analysis was ⅒, clear results were obtained. In the ELISA analysis, even when the protein contents of the samples used in the analysis was ⅕ to ½ compared to those obtained using the above-described antisera, clear results were obtained. Furthermore, all of the anti-human α antibody, anti-mouse α antibody and anti-β antibody had an affinity for antigen not less than 5 times higher than that of the commercially available antibody, and significantly inhibited the interferon-γ production by IL-18 in KG-1 cells ($ND_{50}$ (50% neutralization dose): 0.075 to 0.2 μg/ml: not less than 3 times higher than that of the commercially available antibody).

Recently, an antibody against the IL-18 receptor β subunit was launched in the market (GT Company's 132016 14-P398 (anti-human)). The data sheet thereof states that the antibody permits ELISA, Western blot, and neutralization of IL-18-dependent IFN-γ productivity, and that the $ND_{50}$ is 0.3 to 1.0 μg/ml.

However, it should be noted that the recombinant human IL-18 used by the present inventors used at the time of measuring the neutralizing activity ($ND_{50}$) has an IFN-γ production effect not less than 5 times higher than that of a commercially available rat IL-18 (GT Company) (data not shown). This is thought to be due to a difference in the protein folding occurring at the time of generation of the recombinant IL-18. Therefore, provided that the determination is performed using the recombinant human IL-18 used by the present inventors, the $ND_{50}$ value of GT Company's anti-IL-18 receptor β subunit antibody should be greater than the value shown in the data sheet.

As stated above, all of the anti-α antisera and anti-β antisera prepared in Example 1 could be used for the neutralization of the IFN-γ productivity by IL-18, immunohistochemistry, ELISA, flowcytometry, and immunoprecipitation of tissue specimens, and Western blot of cultured cell samples and tissue extract. Furthermore, the anti-α antibodies and anti-β antibodies elicited by immunization with mixtures of a plurality of peptides were found to be superior to the anti-α antisera and anti-β antisera prepared in Example 1.

Example 3

Expression of IL-18 and IL-18 Receptor in UV-Irradiated Mouse Keratinocytes

In the Example below, the above-described anti-α antibodies and anti-β antibodies were used.

After a wild type mouse (C57/B6: male) had the back shaven, 300 mJ of ultraviolet (UV) was irradiated. Changes in skin thickness in the back of the mouse after the UV irradiation were examined, and the expression of IL-18 and IL-18 receptor was examined by immunohistochemistry using an anti-IL-18 antibody (MBL) and the anti-IL-18 receptor antibodies (anti-α antibodies and anti-β antibodies) prepared in Example 2.

After anesthetization with diethyl ether, the mouse was died from blood loss by cutting the carotid. After the mouse was fixed by perfusion with a phosphate-buffered aqueous solution (pH 7.4) containing 4% para-formaldehyde, the skin (including the dermal layer and subcutaneous tissue) in the back of the mouse was collected. The skin was immersed and fixed in a phosphate-buffered aqueous solution (pH 7.4) containing 4% para-formaldehyde for 48 hours, after which it was dehydrated and immersed in paraffin to obtain paraffin-embedded tissue.

The embedded skin tissue was sliced into sections 4 μm in thickness so that the cross-section was at a right angle with respect to the skin surface, and securely adhered onto a silane-coated slide glass. The following operation was performed on the section securely adhered onto the slide glass.

The section was sequentially immersed in xylene, 100% ethanol, 95% ethanol, 90% ethanol, 80% ethanol, and 70% ethanol to deparaffin and hydrophilicize the section. Subsequently, this section was treated in 0.01% aqueous hydrogen peroxide to inactivate endogenous peroxidase, and washed with distilled water, after which blocking was performed in a phosphate-buffered aqueous solution containing 5% bovine serum albumin (BSA) (liquid A) for 1 hour.

Next, this section was incubated in each primary antibody reaction liquid prepared using the above-described liquid A (containing 5 μg/ml of anti-IL-18 antibody, anti-α antibody or anti-β antibody, respectively) at 4° C. for 24 hours. After the primary antibody reaction, the section was washed with phosphate-buffered aqueous solution, and incubated in a secondary antibody reaction liquid consisting of liquid A containing horseradish peroxidase (HRP)-conjugated anti-goat IgG, anti-mouse IgG, or anti-rabbit IgG (Santa Cruz Company) (1 μg/ml) at room temperature for 3 hours. After the secondary antibody reaction, the section was washed with phosphate-buffered aqueous solution.

Using a 0.05 M Tris-buffered saline containing 20 mg of 3-3-diaminobenzidine (DAB, Katayama Chemical Industries), the section was allowed to develop a color after the above-described reaction. After the color development was stopped, the section was washed, sequentially immersed in ethanol (70%, 80%, 90%, 95% and 100%) and xylene for dehydration, and sealed with cover glass using a soft mount (Wako Pure Chemical).

The results of an examination of the immunohistological specimens obtained using a light microscope are shown in FIG. 1. Immunohistochemistry revealed that at the UV irradiation site, keratinocytes grew to high degrees, and that the expression levels not only of IL-18, but also of the IL-18 receptor α subunit and β subunit increased (6 to 12 days later, 9 to 12 days later, 6 to 9 days later, respectively).

Example 4

Effects of Anti-IL-18 Receptor Antibodies on Mouse Skin Disorder Due to UV Irradiation A wild type mouse (C57/B6: male) had the back shaven, 300 mJ of ultraviolet (UV) was irradiated; 4 days later, anti-IL-18 receptor antibodies (anti-α antibody and anti-β antibody used in mixture) were applied to the UV irradiation site (250 pg/cm$^2$), and 5 days later, skin thickness was measured.

Figure 2:
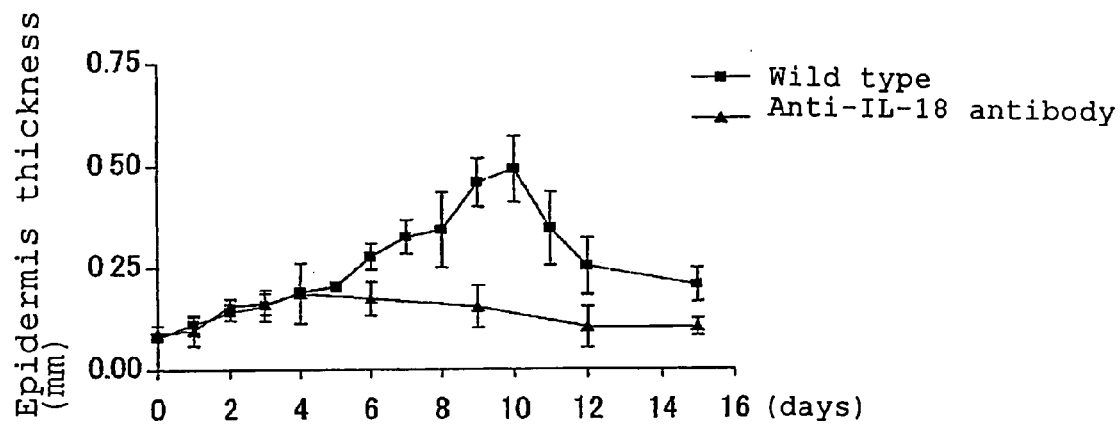
FIG. 2 is a drawing showing courses of epidermal thickening in UV-irradiated mouse epidermis.
Figure 2:
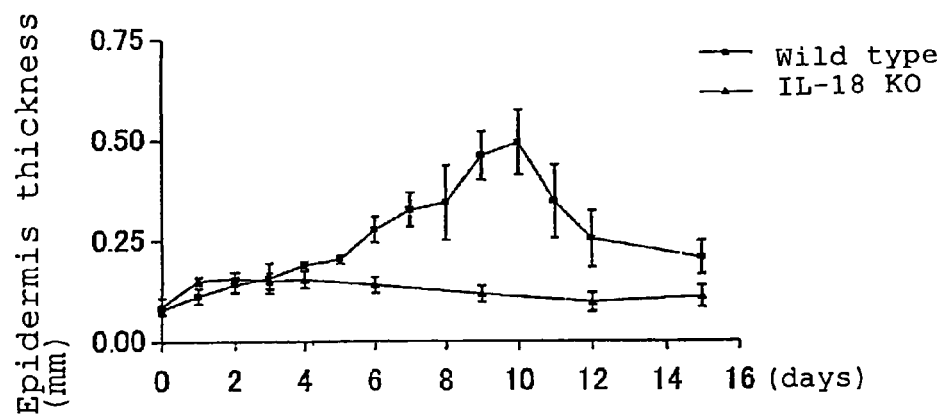

The epidermal thickening observed in untreated mice after 4 days following UV irradiation was suppressed by application of an anti-IL-18 receptor antibody (FIG. 2A).

When UV irradiation was performed on IL-18 knockout (KO) mice in the same manner, epidermal thickening, observed after 4 days following UV irradiation in the wild type, was not seen (FIG. 2B).

These results show that IL-18 is involved in epidermal thickening following UV irradiation, and that the anti-IL-18 receptor antibodies suppress epidermal thickening following UV irradiation.

Next, an examination was performed to determine which of anti-α antibody and anti-β antibody provided the above-described results.

Figure 3:
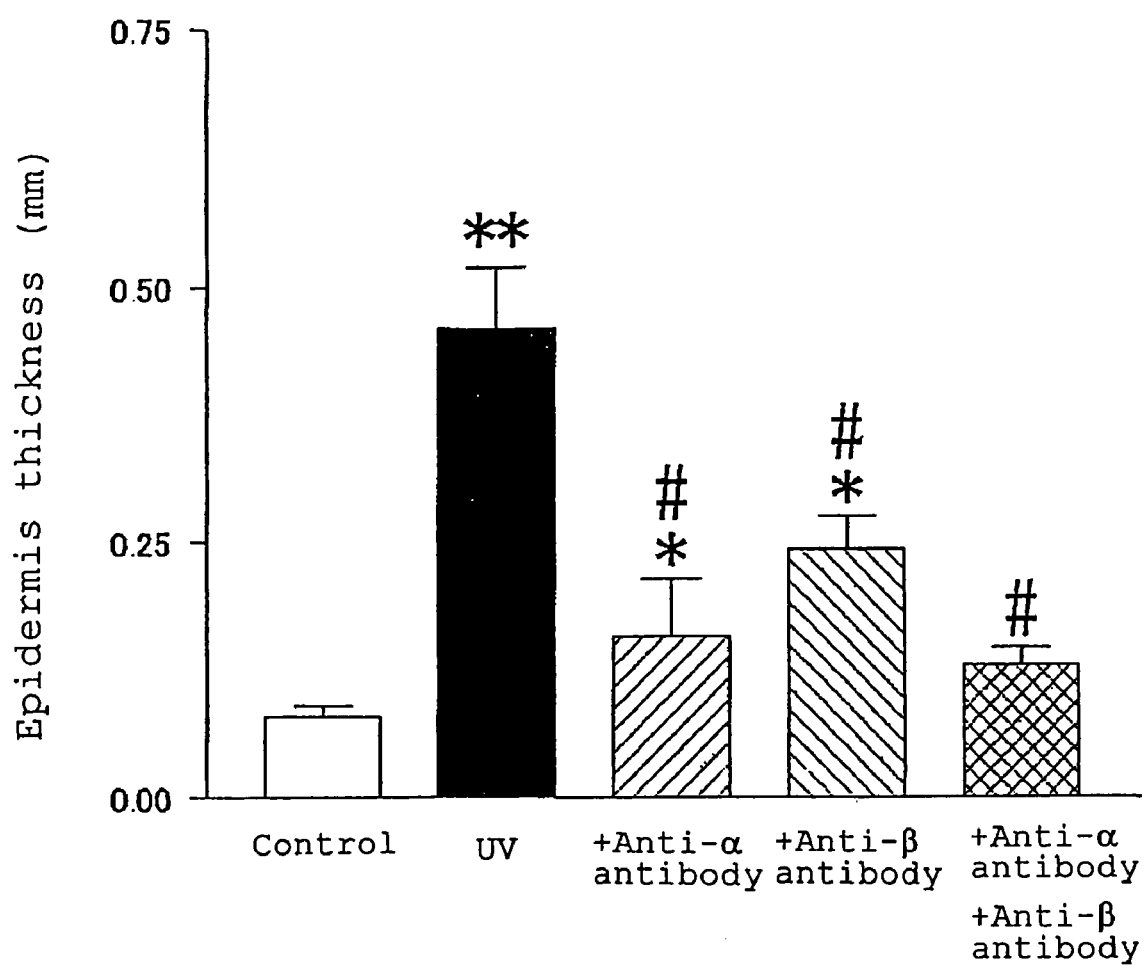
FIG. 3 is a drawing showing the effects of anti-IL-18 antibodies (anti-α antibody and/or anti-β antibody) on epidermal thickening in UV-irradiated mouse epidermis.

As described above, a wild type mouse had the back shaven, and 300 mJ of ultraviolet (UV) was irradiated; 4 days later, an anti-IL-18 receptor antibody (anti-α antibody, anti-β antibody, or mixture) was applied to the UV irradiation site (250 pg/cm$^2$). Although skin thickening at the mouse irradiation site was suppressed whatever the anti-IL-18 receptor antibody used, the anti-α antibody was more effective than the anti-β antibody (FIG. 3). In the mixed application of the anti-α antibody and the anti-β antibody, the thickness before UV irradiation was maintained; the mixed application was found to be the most effective.

Example 5

Changes in Mouse Keratinocytes Due to Ultraviolet Irradiation

After a mouse had the back shaven, 300 mJ of ultraviolet (UV) was irradiated; after the irradiation, the processes of is skin loss, thickening, and repair were examined with a focus on keratinocytes.

When ultraviolet was irradiated to a wild type mouse (C57/B6: male), the following changes were observed in the epidermis:

1) Early changes (observed within 24 hours)
  (a) Swelling and reddening of epidermis
  (b) Apoptotic epidermal keratinocyte layer loss 2) Midterm changes (observed on days 2 to 5)
  (c) Occurrence of epidermal keratinization and desquamation
  (d) Increase in expression levels of IL-18 receptor protein and IL-18 protein
  (e) Activation of growth and/or differentiation of keratinocytes, and accompanying epithelial thickening 3) Late changes (observed on days 5 to 15)
  (f) Epithelial thickening (reached a peak on day 10)
  (g) Hair re-development (after day 12).

Likewise, when ultraviolet was irradiated to IL-18 (−/−) mice (C57/B6 background: male), the above-described (b) was remarkably increased, but (c), (e), and (f) were mild and (g) was observed on days 4 to 6.

Example 6

Figure 4:
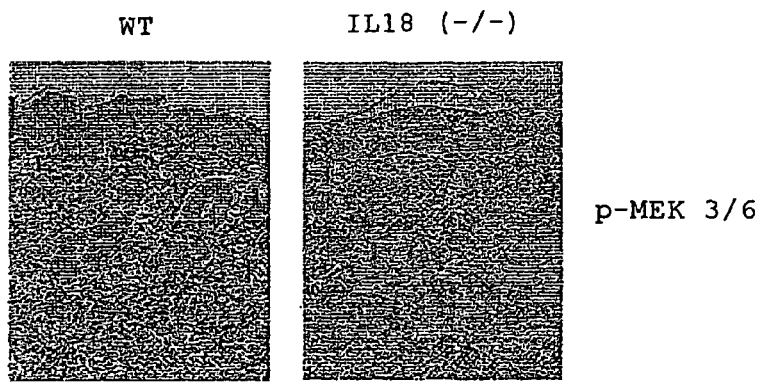
FIG. 4 is a drawing showing the activation of p38 MAPK in UV-irradiated mouse epidermis. Results with IL-18 (−/−) mice (C57/B6 background: male) are shown in FIG. 4A. In the wild type, the phosphorylation of MEK3/6 and p38 MAPK occurred, whereas in the IL-18 KO mice, the phosphorylation of MEK3/6 and p38 MAPK did not occur, and the expression level of cyclin D1 decreased compared to the wild type (FIG. 4B). Furthermore, the IL-18-dependent activation of MEK3/6 and p38 MAPK and the expression of cyclin D1 due to UV irradiation were suppressed by applying an anti-IL-18 receptor antibody to the irradiation site (FIG. 4B).
Figure 4:
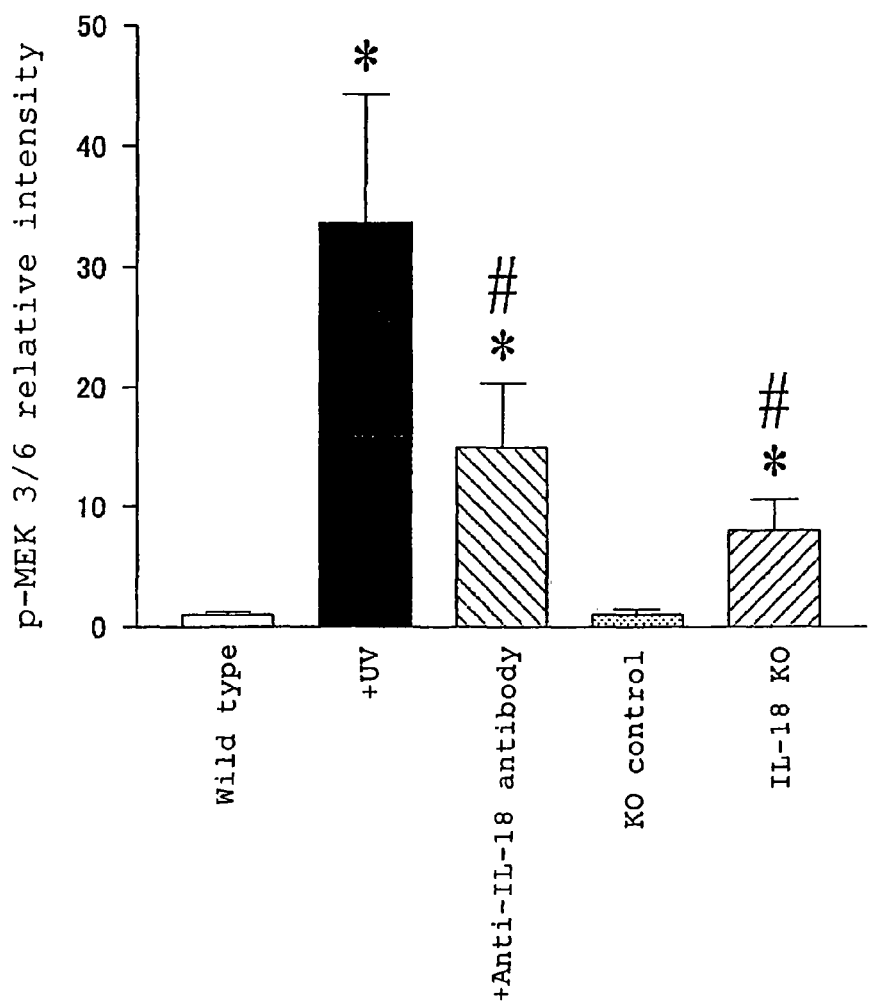
Figure 5:
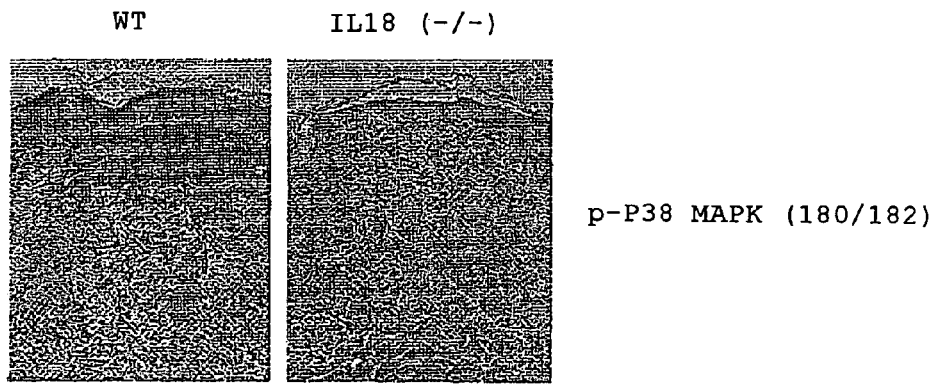
FIG. 5 is a drawing showing the activation of MEK3/6 in UV-irradiated mouse epidermis. Results with IL-18 (−/−) mice (C57/B6 background: male) are shown in FIG. 5A. In the wild type, the phosphorylation of MEK 3/6 and p38 MAPK occurred, whereas in the IL18 KO mice, the phosphorylation of MEK 3/6 and p38 MAPK did not occur, and the expression level of cyclin D1 decreased compared to the wild type (FIG. 5B). Furthermore, the IL-18-dependent activation of MEK3/6 and p38 MAPK and the expression of the cyclin D1 due to UV irradiation were suppressed by applying an anti-IL-18 receptor antibody to the irradiation site (FIG. 5B).
Figure 5:
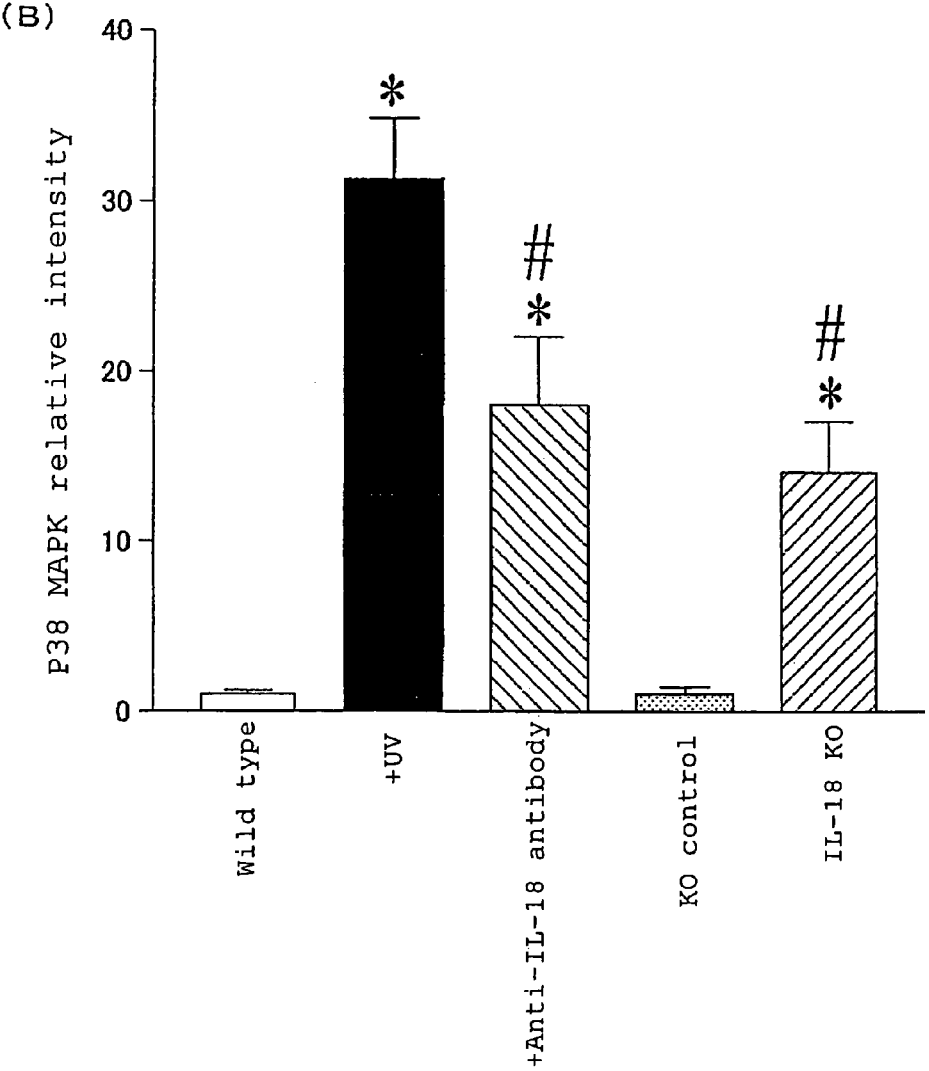
Figure 6:
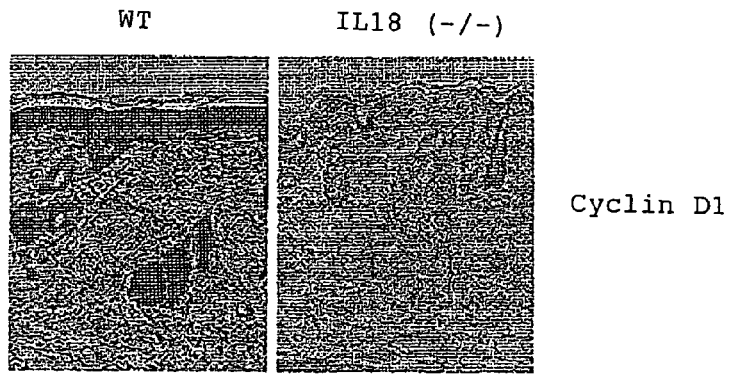
FIG. 6 is a drawing showing the expression of cyclin D1 in UV-irradiated mouse epidermis. Results with IL18(−/−) mice (C57/B6 background:male) are shown in FIG. 6A. In the wild type, the phosphorylation of MEK3/6 p38 MAPK occurred, whereas in the IL-18 KO mice, the phospholylation of MEK3/6 and p38 MAPK did not occur, and the expression level of cyclin D1 decreased compared to the wild type (FIG. 6B). Furthermore, the IL-18-dependent activation of MEK3/6 and p38 MAPK and the expression of cyclin D1 due to UV irradiation were suppressed by applying and anti-IL-18 receptor antibody to the irradiation site (FIG. 6B).
Figure 6:
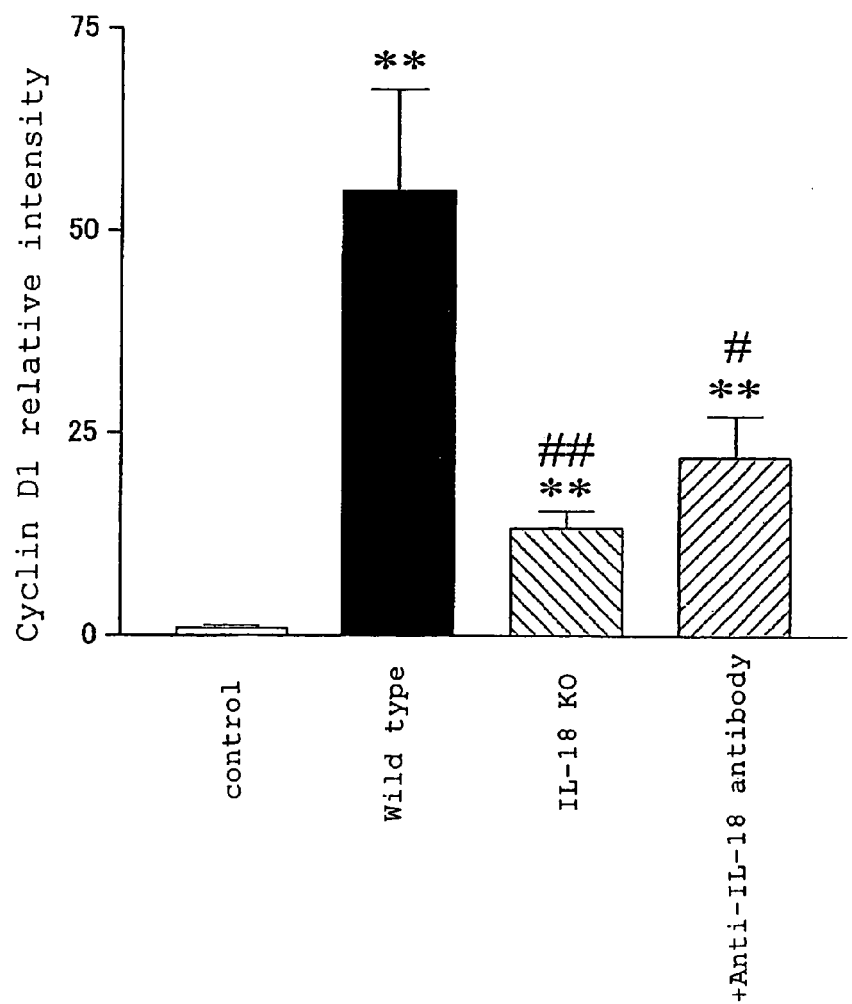

Activation of Intracellular Signal Transduction Molecules at UV Irradiation Site In the skin of wild type mice (C57/B6: male) after UV irradiation, signal transduction molecules involved in growth and/or differentiation (MEK3/6 and p38 MAPK) accumulate along with skin thickening. Also, in the skin after the UV irradiation, cyclin D1, which is a cell cycle marker protein, is highly produced. However, in IL-18 (−/−) mice (C57/B6 background: male), these phenomena are not observed (FIG. 4A, FIG. 5A and FIG. 6A). These facts suggested that in the keratinocytes after UV irradiation, the signal transduction pathway mediated by MEK3/6 and p38 MAPK might be activated IL-18-dependently to express cyclin D1, and that the growth and/or differentiation of the keratinocytes might be controlled. Hence, in the UV-irradiated wild type and IL-18 KO mice, using an antibody against MEK3/6, an antibody against p38 MAPK (both anti-phosphorylated protein antibodies that recognize the activated form), and an antibody against cyclin D1, the activation of these signal transduction molecules in the keratinocytes at the UV irradiation site was examined.

In the same manner as Example 3, changes in mouse back skin thickness after the UV irradiation were examined, and immunohistochemical specimens concerning the above-described signal transduction molecules were prepared.

Specifically, except that an anti-cyclin D1 antibody (400 fold, cell signaling technology), an anti-phosphorylated MEK3/6 antibody (400 fold, SantaCruz), an anti-p38 MAPK antibody (100 fold, Cell Signaling Technology) and an anti-phosphorylated p38 MAPK antibody (400 fold, Cell Signaling Technology) were used as the primary antibodies, immunohistological specimens were prepared in the same manner as the technique performed in Example 3.

In the wild type, the phosphorylation of MEK3/6 and p38 MAPK occurred, whereas in the IL-18 KO mice, the phosphorylation of MEK3/6 and p38 MAPK did not occur, and the expression level of cyclin D1 decreased compared to the wild type (FIG. 4B, FIG. 5B and FIG. 6B).

Furthermore, the IL-18-dependent activation of MEK3/6 and p38 MAPK and the expression of cyclin D1 due to UV irradiation were suppressed by applying an anti-IL-18 receptor antibody to the irradiation site (FIG. 4B, FIG. 5B and FIG. 6B).

From the results above, it was shown that at the UV irradiation site of mouse keratinocytes, the IL-18-dependent activation of MEK3/6 and p38 MAPK and the expression of cyclin D1 occurred, and as a result the growth and/or differentiation of the keratinocytes occurred.

Example 7

Effect of IL-18 Receptor Antagonist on Hair Re-Growth at UV Irradiation Site

In the same manner as Example 3, after wild type mice (C57/B6: male) and IL-18 (−/−) mice (C57/B6 background: male) had the back shaven, 300 mJ of ultraviolet (UV) was irradiated; immediately after the UV irradiation, an anti-IL-18 antibody was applied to the irradiation site or administered intraperitoneally.

Mouse back skin (2×2.6 cm) after the UV irradiation was collected periodically. Each skin specimen collected was divided into 2-mm squares under a stereoscopic microscope, and the percentage of hair growth area in each division was examined microscopically. The percentages of hair growth areas in all divisions were statistically processed, and the data were evaluated to determine the percentage of hair growth area in the skin specimen.

Figure 7:
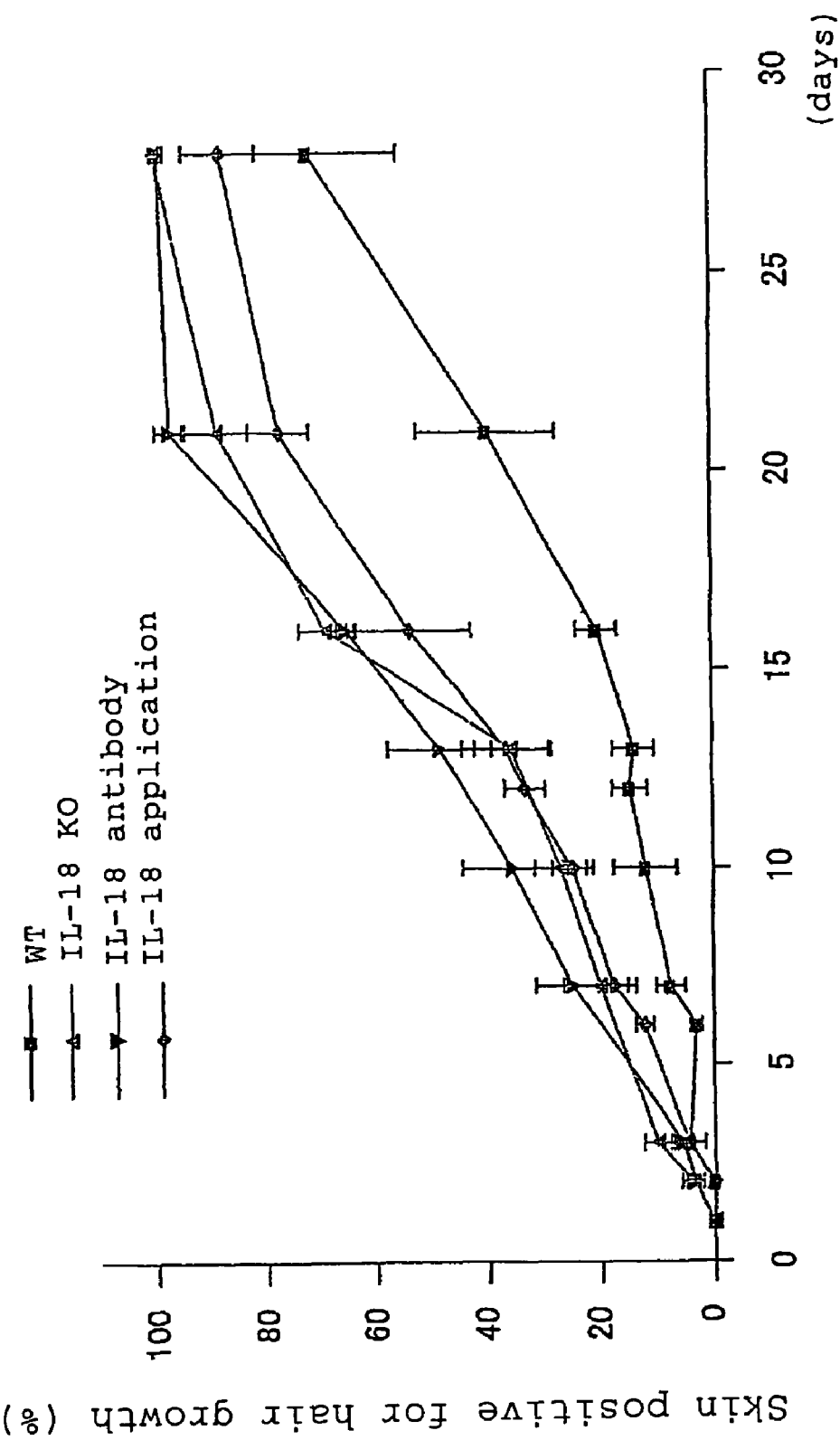
FIG. 7 is a drawing showing the effect of an anti-IL-18 antibody on hair growth occurring in UV-irradiated mouse epidermis.

At the UV irradiation sites of the mice applied with the anti-IL-18 receptor antibody immediately after the UV irradiation (250 pg/cm$^2$), hair re-growth was promoted. Specifically, hair re-growth observed after 12 days following UV irradiation was observed 7 days after the UV irradiation with the application of the anti-IL-18 receptor antibody. Similar results were obtained by intraperitoneal administration at 2000 pg/mouse (FIG. 7).

The above-described results show that by inhibition of the function of IL-18, hair growth is promoted.

Comparing the effects of the application and intraperitoneal administration in this Example, intraperitoneal administration was slightly more effective, but the effects differed by changing the base used for application. From this fact, a similar effect to that obtained with intraperitoneal administration can be expected, provided that a base is chosen, even in the case of application.

Example 8

Effect of IL-18 on Cultured Human Keratinocytes

Commercially available human keratinocyte KG-1 cells (Cambrex Company, USA) were sown to a 6 cm plate in diameter having a keratinocyte growth medium (Kurabo Industries) dispensed thereto ($2 \times 10^5$ cells/plate). The cells were grown for 10 days, after which recombinant IL-18 was added to the medium (final concentration 500 pg/ml). As the recombinant IL-18, the recombinant protein described in J. Immunol. 156: 4274-9 (1996) and Nature 378: 88-91 (1995) was used. Without the addition of the recombinant IL-18 or with the addition of PBS, apoptosis due to contact inhibition was induced in the keratinocytes. However, when IL-18 was added, apoptosis due to contact inhibition was suppressed for at least 10 more days (results not shown).

Figure 8:
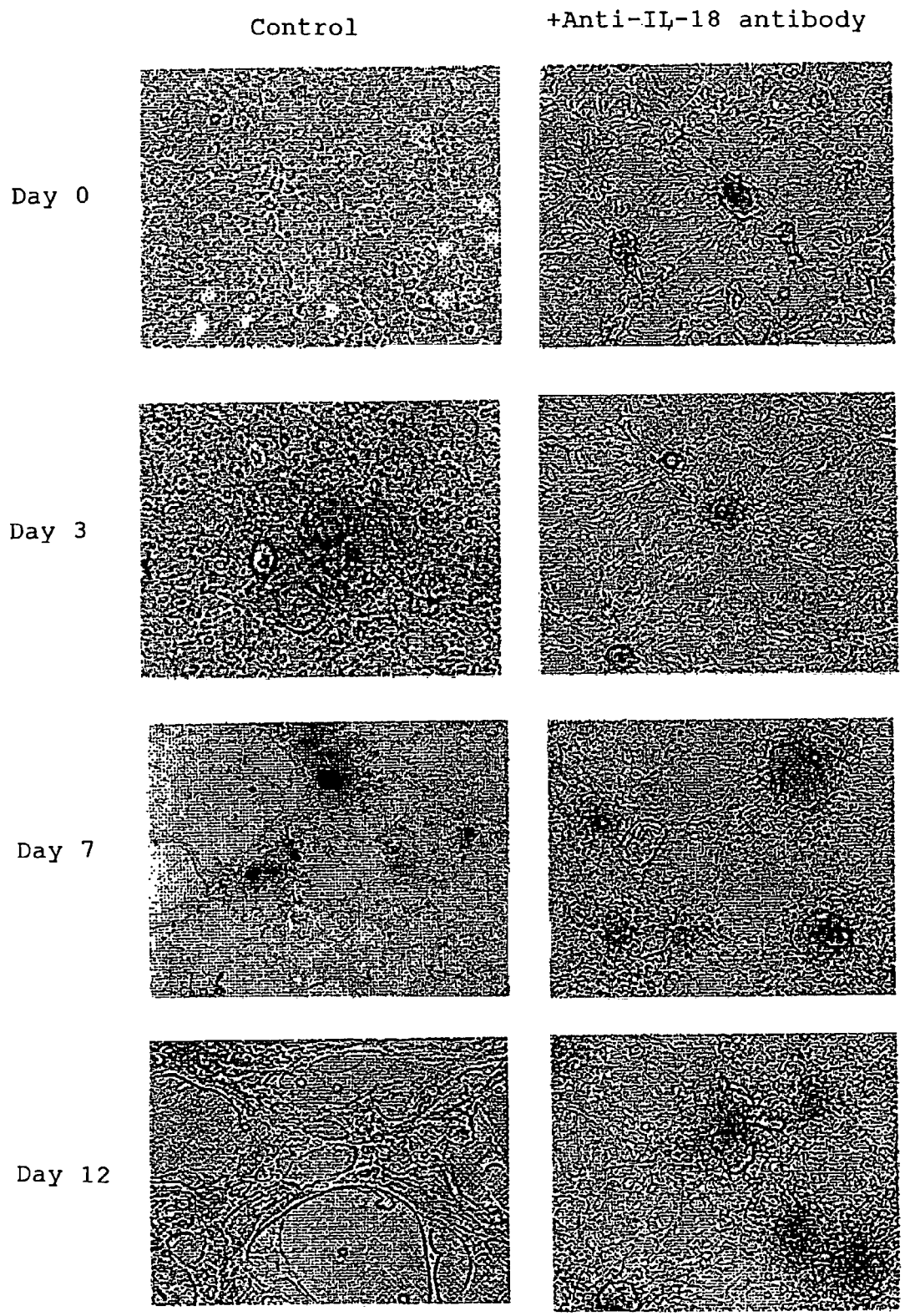
FIG. 8 is a drawing showing the effects of an anti-IL-18 antibody on the differentiation process of cultured human keratinocytes.

Next, the effect of IL-18 on differentiated keratinocytes was examined. As described above, KG-1 cells were sown to a 6 cm plate in diameter having a keratinocyte growth medium (Kurabo Industries) dispensed thereto ($2 \times 10^5$ cells/plate). After the cells were grown for 6 days until they reached 70% confluency, 1.2 mM $CaCl_2$ was added to the medium, and the cells were allowed to differentiate. When an anti-IL-18 antibody (MBL Company) was added to the medium (final concentration 1 μg/ml) at the time of differentiation induction, apoptosis of differentiated keratinocytes observed without the addition of anti-IL-18 antibody was suppressed (FIG. 8).

Figure 9:
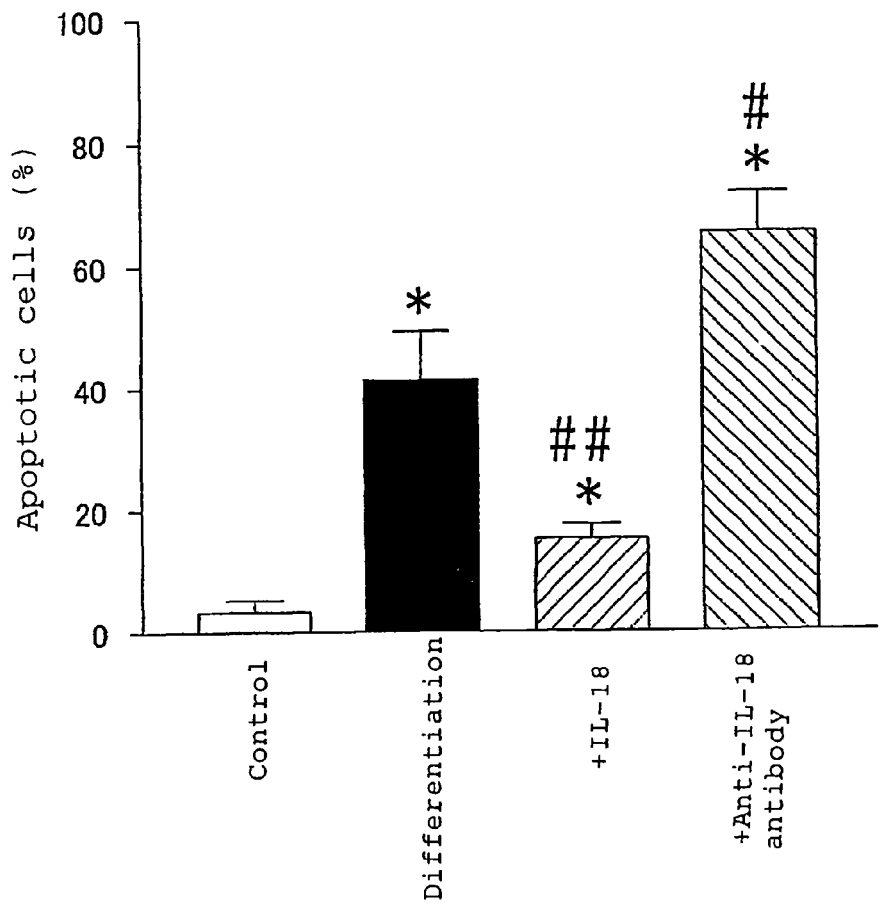
FIG. 9 is a drawing showing the effect of IL-18 or an anti-IL-18 antibody on apoptosis occurring in the differentiation stage of cultured human keratinocytes.

At the time of differentiation induction, IL-18 (final concentration 500 pg/ml) or an anti-IL-18 antibody (final concentration 500 pg/ml) was added to the medium; 12 days later, TUNEL-stained cells were counted, and the number of cells having apoptosis induced therein was calculated. The results are shown in FIG. 9.

Without the addition of IL-18 or the anti-IL-18 antibody or with the addition of PBS (negative control), in the differentiated keratinocytes, cells having apoptosis induced therein (apoptotic cells) were observed even after day 12 following differentiation induction were observed, but when IL-18 was added, the number of apoptotic cells observed decreased significantly.

Also, when the anti-IL-18 antibody was added, the number of apoptotic cells observed increased significantly. When the differentiation of keratinocytes was induced, IL-18 was produced in a large amount and secreted in the culture supernatant (results not shown). Therefore, it can be thought that the anti-IL-18 antibody inhibited the function of IL-18 secreted with the differentiation induction of keratinocytes.

From the results above, it was shown that IL-18 inhibited apoptosis induced in human keratinocytes, whether in undifferentiated state or differentiated state.

Example 9

Effect of IL-18 on UV-Dependent or Radiation-Dependent Apoptosis of Keratinocytes As shown in Example 8, apoptosis in cultured keratinocytes was suppressed by IL-18. Hence, the effect of IL-18 on apoptosis dependent on DNA damage due to UV in UV-irradiated mouse keratinocytes was examined.

A skin section prepared in the same manner as Example 3 was subjected to a proteolytic treatment using Proteinase K liquid at 37° C. for 5 minutes. After the section was washed with PBS(−), the DNA terminus exposed due to fragmentation by apoptosis was labeled in TdT liquid (at 37° C. for 2 hours). After washing, this section was incubated in a reaction liquid comprising an HRP-conjugated anti-TdT antibody (at 37° C. for 30 minutes) to bind peroxidase to the DNA cleavage end resulting from apoptosis. After incubation, the section was washed, and allowed to develop a color in the same manner as Example 3, after which it was dehydrated and embedded.

An evaluation of the number of apoptosed cells was performed by TUNEL staining. Using an apoptosis detection kit (Wako Pure Chemical) according to the instructions thereof, TUNEL staining was performed. The number of apoptotic cells can be counted as TUNEL staining-positive cells. The number of apoptotic cells was obtained by counting six visual fields in the same section under a light microscope (×100), and the mean number for the six visual fields was used as the number of apoptotic cells in the section.

Figure 10:
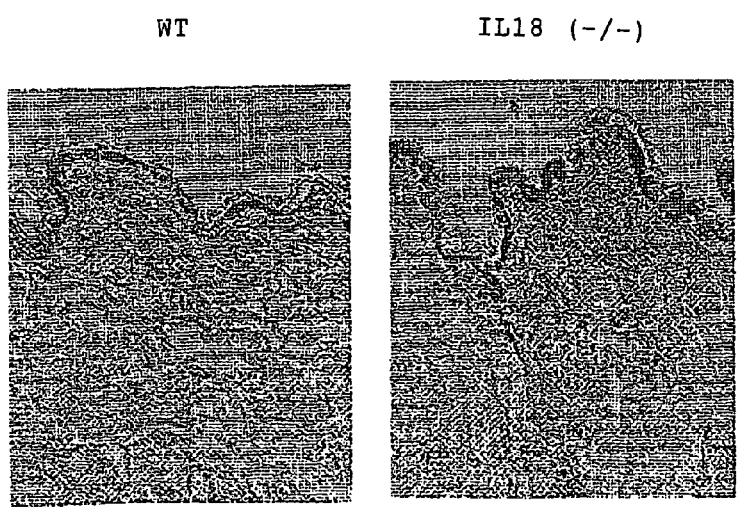
FIG. 10 presents immunohistochemical specimens showing apoptotic keratinocytes induced occurring in UV-irradiated mouse epidermis.

As shown in Example 5, when ultraviolet was irradiated to wild type mice (C57/B6: male), an apoptotic loss of epidermal keratinocyte layer ((b) above) was observed as an early change in the epidermis (observed within 24 hours), and when ultraviolet was irradiated to IL-18 (−/−) mice (C57/B6 background: male), this phenomenon was remarkably enhanced (FIG. 10).

Figure 11:
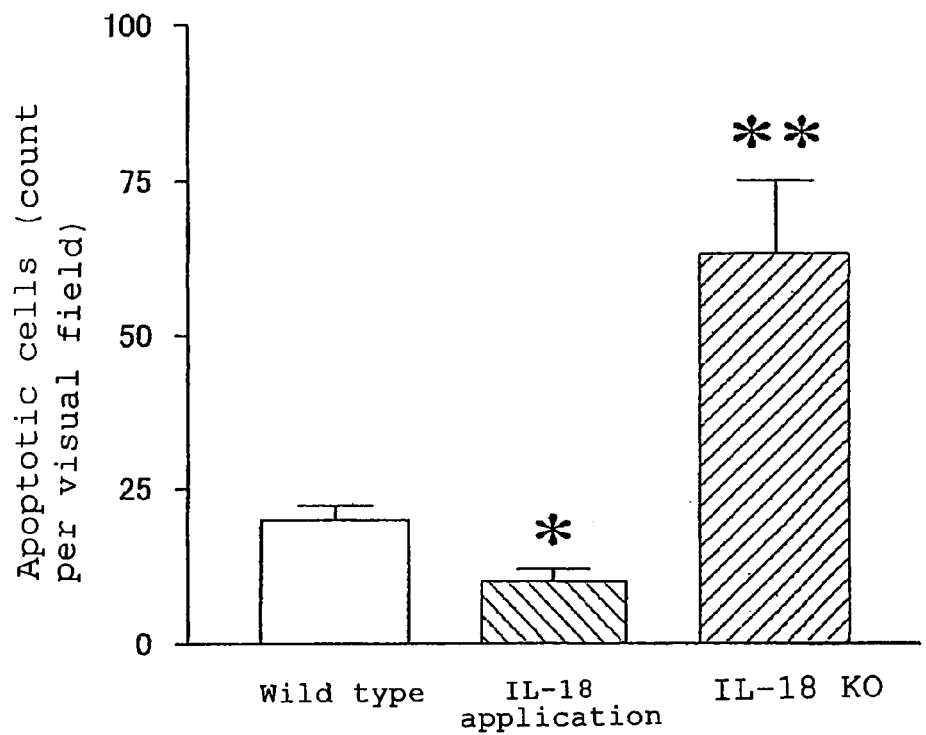
FIG. 11 is a drawing showing the effect of IL-18 on apoptosis of keratinocytes in UV-irradiated mouse epidermis. In the mice having IL-18 applied (500 pg/cm$^2$) immediately after the UV irradiation, apoptotic cells decreased significantly (FIG. 11A). Similar results were obtained by application at 250 pg/cm$^2$ and intraperitoneal administration at 2000 pg/mouse. Also, in the IL-18 KO mice, the induction of apoptosis by UV irradiation occurred at high levels (FIG. 11A). Radiation (4 Gray) was irradiated in place of UV, and apoptotic cells were examined in the same manner. In the mice applied (500 pg/cm$^2$) with IL-18 immediately after radiation irradiation, apoptotic cells decreased significantly (FIG. 11B). Similar results were obtained by intraperitoneal administration at 1500 pg/mouse. Also, in the IL-18 KO mice, the induction of apoptosis by UV irradiation occurred at high levels (FIG. 11B).
Figure 11:
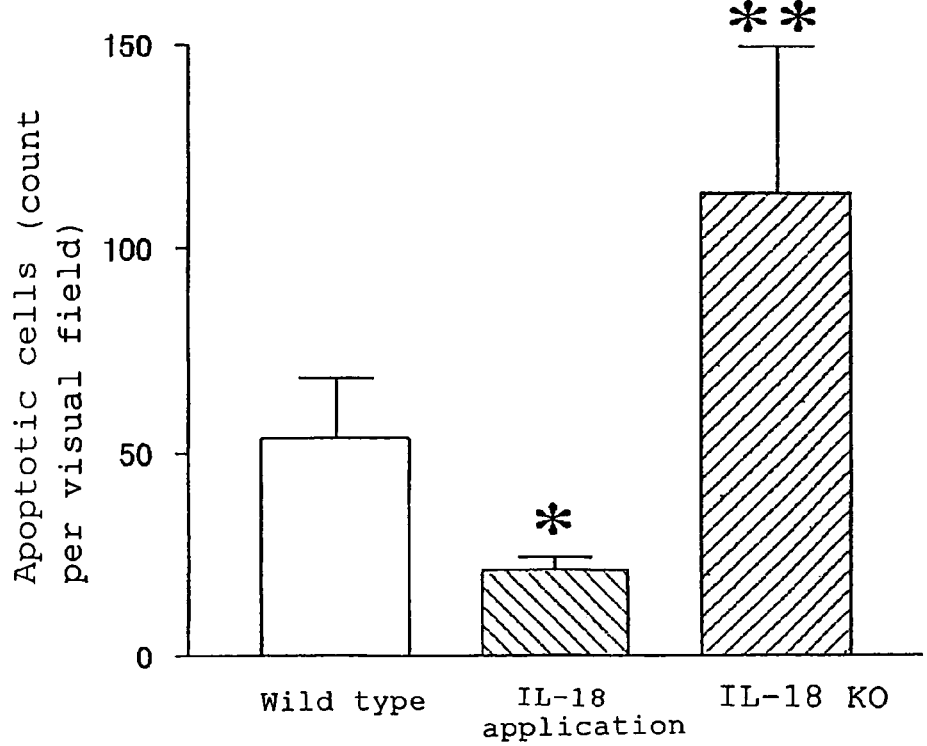

In the mice having IL-18 applied (500 pg/cm$^2$) immediately after the UV irradiation, apoptotic cells decreased significantly (FIG. 11A). Similar results were obtained by application at 250 pg/cm$^2$ and intraperitoneal administration at 2000 pg/mouse. Also, in the IL-18 KO mice, the induction of apoptosis by UV irradiation occurred at high levels (FIG. 11A).

Radiation (4 Gray) was irradiated in place of UV, and apoptotic cells were examined in the same manner. In the mice applied (500 pg/cm$^2$) with IL-18 immediately after radiation irradiation, apoptotic cells decreased significantly (FIG. 11B). Similar results were obtained by intraperitoneal administration at 1500 pg/mouse. Also, in the IL-18 KO mice, the induction of apoptosis by UV irradiation occurred at high levels (FIG. 11B).

These results show that using IL-18, epithelial skin disorders to the skin caused by UV or radiation (particularly apoptotic loss of epithelium) can be prevented and/or treated.

For mouse skin disorders after UV irradiation, recombinant IL-18 was applied or intraperitoneally administered, and the effects thereof were examined. Specifically, when IL-18 was applied to the skin (250 pg/cm$^2$) or intraperitoneally administered (1000 pg/mouse) to mice immediately after the UV irradiation, all of the changes (a) to (g) shown in Example 6, except the occurrence of desquamation, mitigated.

When IL-18 at the above-described concentration was applied for a long time (3 weeks or more), slight skin thickening not accompanied by skin hardening occurred (desquamation due to promoted keratinocyte differentiation was prevalent). However, skin disorders due to UV irradiation were slightly mitigated.

From the results above, it was shown that it was appropriate to apply or intraperitoneally administer a low concentration of IL-18 immediately after irradiation of UV or radiation.

Example 10

Effects of IL-18 on Stress-Related Disease

It has been shown to date that the nervous system, the endocrine system and the immune system interact with each other to constitute a major host defense network. It has been proposed that controlling these interactions could be an important therapeutic strategy for autoimmune disease and inflammatory disease. The present inventor found that IL-18 was involved in the interactions among the nervous system, the endocrine system and the immune system.

The involvement of nitrogen oxide (NO) on mouse plasma IL-18 was examined. Mice (wild type or iNOS (NO synthase) knockout mice) were given restraint stress, and NO2/3 levels and IL-18 levels in plasma were examined. Also, the time course of plasma IL-18 level in iNOS knockout mice injected with recombinant IL-18 were examined. In the wild type mice, the NO2/3 concentration in plasma rose, whereas in the iNOS knockout mice, the concentration did not rise. In the wild type mice, the IL-18 level in plasma rose from 50 pg/ml to 1000 pg/ml, and in the iNOS knockout mice, the level rose to 3000 pg/ml. From the results of immunoblotting, the IL-18 protein in plasma was the 18-kD activated form. When changes in plasma IL-18 level were compared between the iNOS knockout mice and the wild type mice, there was a difference in the reduction in plasma IL-18 level.

From the results above, it was shown that (1) in mice exposed to restraint stress, the NO2/3 concentration in plasma rose, and that (2) in mice exposed to restraint stress, the activated form IL-18 level in plasma rose. iNOS was found to particularly inhibit the upregulation of stress-induced plasma IL-18 levels.

Furthermore, the effect of restraint stress on mouse plasma IL-18 level was examined. The effects of ACTH and anti-ACTH antibody on plasma IL-18 levels in stressed mice were also examined. Using immunoblotting, IL-18 proteins in plasma and in the adrenal were characterized. Due to restraint stress, IL-18 protein levels in plasma and in the adrenal increased (>1000 pg/ml). The anti-ACTH antibody significantly suppressed the above-described increase in the level of IL-18 protein. With ACTH administration, the IL-18 protein level in the adrenal increased, but with the induction of ACTH per se, the IL-18 protein level in plasma did not rise. From the results of immunoblotting, it was found that the IL-18 protein in the adrenal was mainly the 24-kD inactivated form, and the IL-18 protein in plasma was the 18-kD activated form.

From the results above, it was shown in mice exposed to restraint stress that (1) activated form IL-18 was upregulated via the HPA axis in plasma, that (2) in the adrenal, inactivated form (24 kD) IL-18 was induced, cleaved and secreted in blood as the 18-kD activated form, and that (3) the cleavage from the inactivated form to the activated form was an important factor concerning the upregulation of IL-18 in plasma. Hence, it was shown that IL-18 was involved in the interactions among the nervous system, the endocrine system and the immune system.

Example 11

Effect of NADPH Oxidase Antagonist on Plasma IL-18 Concentration with Stress Load

Figure 12:
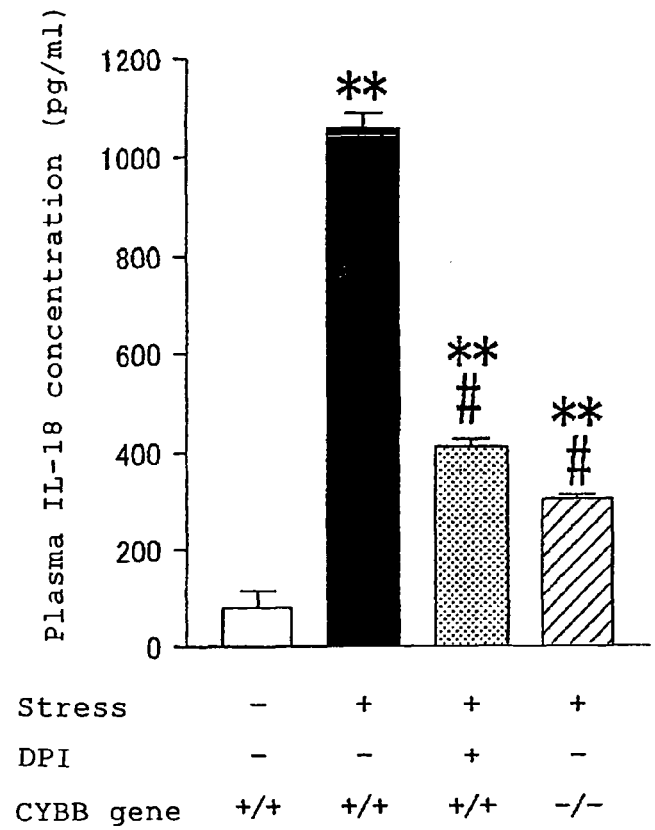
FIG. 12 is a drawing showing the effects of an NADPH oxidase antagonist on mouse plasma IL-18 concentration under stress loading.

Wild type mice (C57/B6: male) and CYBB (NADPH oxidase gene) (−/−) mice (C57/B6 background: male) were restrained in plastic tubes (27 millimeters in diameter) for 6 hours, after which cardiac blood was drawn under anesthesia. Plasma was collected via centrifugation, and IL-18 concentrations in plasma were measured using an ELISA method (Quantikine R&D Company). To one group of wild type mice, 1 hour after the start of stress loading, DIPHENYLE-NEIODNIUM (DPI: NADPH oxidase inhibitor) was administered intraperitoneally at 30 µg/animal, and the effect thereof was examined (FIG. 12).

The elevation of IL-18 concentration in plasma was suppressed to 400 pg/ml by DPI administration in the wild type, but in the mice lacking the CYBB gene, it remained at 300 pg/ml. These results show that by suppressing NADPH oxidase, the stress-dependent elevation of plasma IL-18 can be suppressed. Also, regarding the elevation of plasma IL-18 due to stress, it was shown that the NADPH oxidase antagonist, which is an antagonist of active oxygen, functioned as a suppressant.

(**; $p<0.001$ (versus non-stressed control), #; $p<0.01$ (versus stress-loaded wild type), n=9).

Also, a similar experiment was performed by intravenous injection, and similar results were obtained (data not shown).

Example 12

Effect of anti-IL-18 Receptor Antibody on Stress-Dependent Elevation of Serum IL-6 Level

Figure 13:
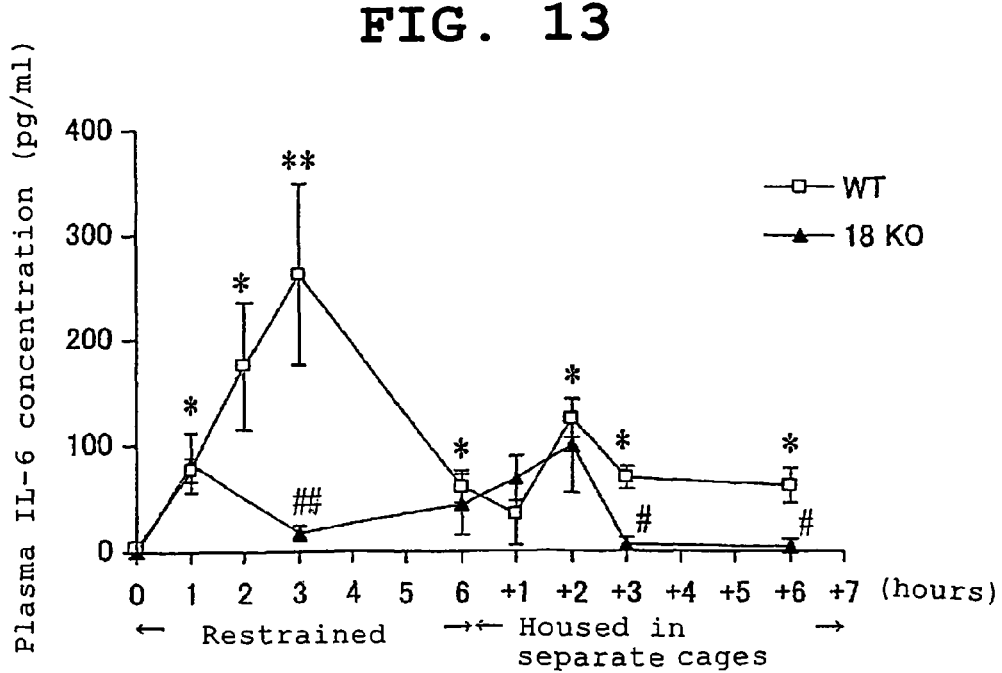
FIG. 13 is a drawing showing the effects of an anti-IL-18 receptor antibody on serum IL-6 level elevation under stress loading.

Wild type mice (C57/B6: male) and IL-18 (−/−) mice (C57/B6 background: male) were restrained by the same method as Example 11, after which they were liberated individually into cages. Six hours after the liberation, serum was collected by the same method as Example 11, and IL-6 concentrations in serum were measured (FIG. 13).

It was shown that in the IL-18 (−/−) mice, the elevation of IL-6 in serum was at an extremely low level, and that IL-18 was involved in the stress-dependent elevation of serum IL-6 level.

Note that although the data are not shown in the figure, the elevation of IL-6 level caused by 3 hours of stress was suppressed by intraperitoneally administering anti-IL-18 receptor antibodies (anti-α antibody+anti-β antibody) at 25 µg/kg 10 minutes before stress loading.

(**; $p<0.001$, *; $p<0.01$ (versus non-stressed wild type), ##; $p<0.001$, #; $p<0.01$ (versus non-stressed wild type at the same time points), n=4 to 9).

Example 13

Stress-Dependent Elevation of Serum IL-18 Level in Disease Model Mice

Figure 14:
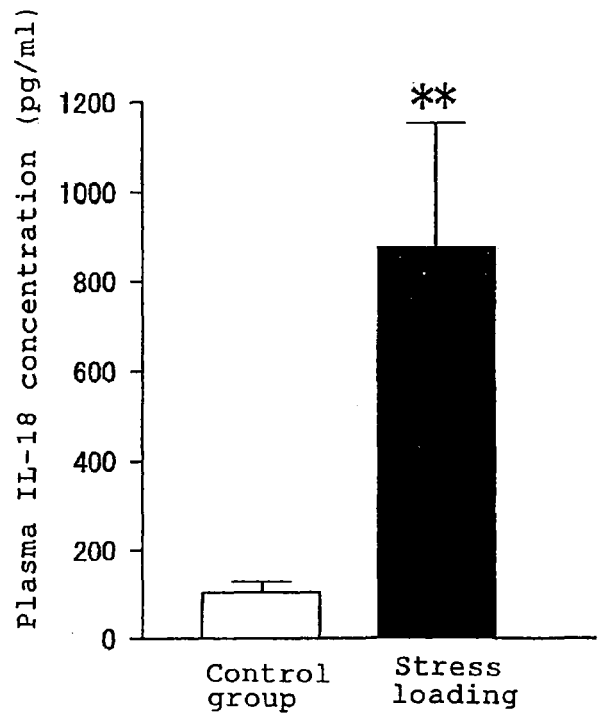
FIG. 14 is a drawing showing the stress-dependent elevation of serum IL-18 level in a mouse model of systemic lupus erythematosus.

As mice that spontaneously develop nephritis and/or arthritis and the like, MRL/lpr mice (Charles River Japan Inc., 12 weeks), which are widely recognized as a mouse model of systemic lupus erythematosus, were loaded with stress in the same manner as Example 11, after which serum IL-18 levels were examined (FIG. 14).

In the MRL/lpr mice, an stress-dependent elevation of serum IL-18 level was observed. Although the data are not shown in the figure, this elevation, as in the wild type mice, was suppressed by SOD, DPI, a p38 MAPK inhibitor, a caspase 1 inhibitor, and a caspase 11 inhibitor.

(**; $p<0.01$ (versus non-stressed control), n=6)

Example 14

Stress-Dependent Elevation of Plasma IL-6 Level in Disease Model Mice

Figure 15:
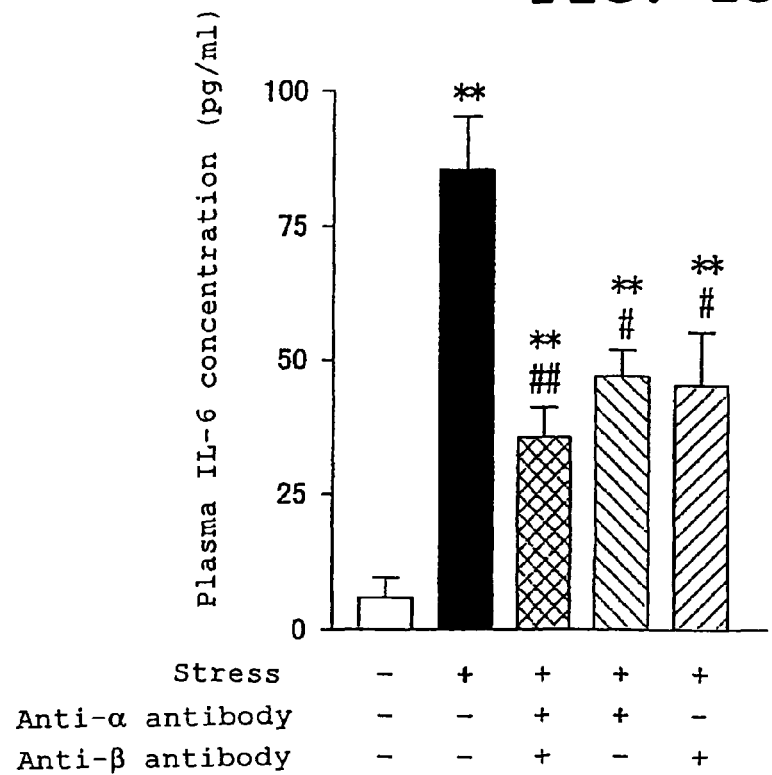
FIG. 15 is a drawing showing the effects of anti-IL-18 receptor antibodies on the stress-dependent elevation of plasma IL-6 level in a mouse model of systemic lupus erythematosus.

The MRL/lpr mice (12 weeks) used in Example 13 were loaded with 3 hours of stress, after which plasma IL-6 levels were examined. Furthermore, a variety of anti-IL-18 receptor antibodies were administered 10 minutes before the start of restraint, and the effects of these antibodies were examined. As the anti-IL-18 receptor antibodies, an anti-α antibody, an anti-β antibody, and mixtures thereof were used (FIG. 15).

Although the plasma IL-6 level rose due to stress, this elevation of plasma IL-6 level was suppressed by intraperitoneally administering anti-IL-18 receptor antibodies (anti-α antibody+anti-β antibody) at 25 µg/kg 10 minutes before stress loading. Although suppression was obtained by administration of the anti-α antibody or anti-β antibody alone, administration of the mixture was more effective.

Example 15

Effect of Anti-IL-18 Receptor Antibodies on the Stress-Dependent Elevation of Urinary Albumin Level in Disease Model Mice

Figure 16:
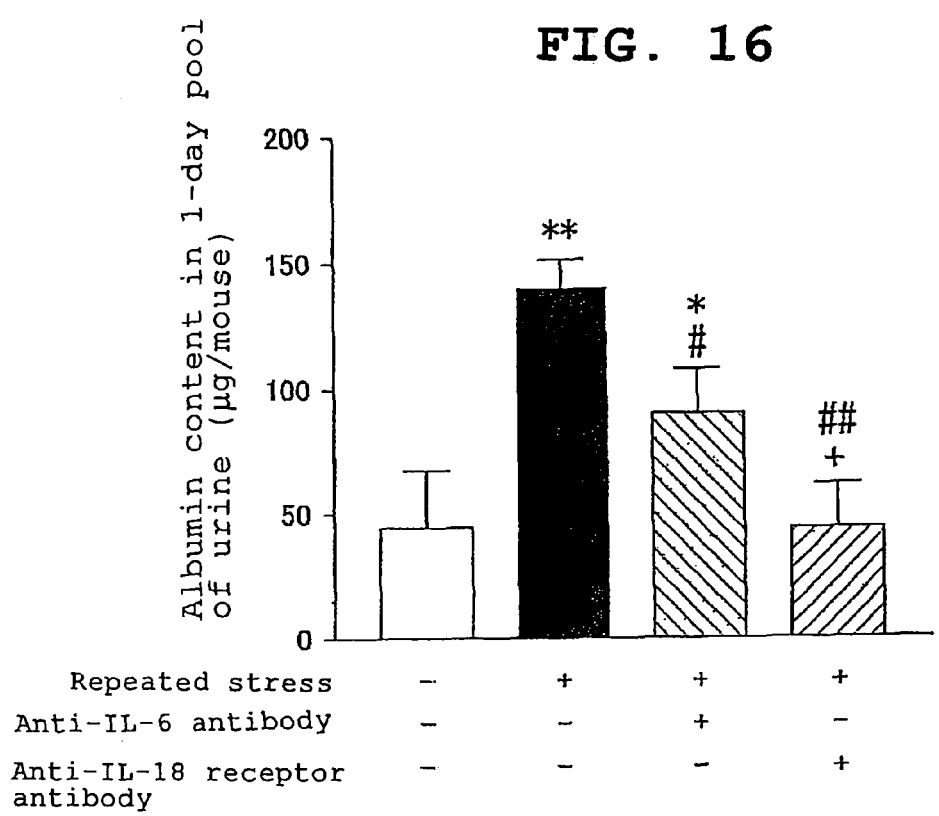
FIG. 16 is a drawing showing the effects of an anti-IL-6 antibody or an anti-IL-18 receptor antibody on the stress-dependent elevation of urinary albumin level in a mouse model of systemic lupus erythematosus.

The MRL/lpr mice used in Example 13 (12 weeks) were stressed for 3 hours every two days for 3 weeks, and albumin contents in one-day pool of urine after the stress loading were measured. Also, 10 minutes before the start of restraint, anti-IL-18 receptor antibodies (anti-α antibody+anti-β antibody) were intraperitoneally administered at 25 µg/kg, and the effects of the antibodies were examined. Furthermore, an anti-IL-6 antibody (Santa Cruz Company, SC1265) was administered, and its effect was examined (FIG. 16).

In the MRL/lpr mice, the urinary albumin content rose due to stress loading, and the urinary albumin content in the antibody administration group was suppressed. The urinary albumin content in the anti-IL-18 receptor antibody administration group was lower than that in the anti-IL-6 antibody administration group, and this was similar to the level in the non-stress-loaded group.

(**; $p<0.01$, *; $p<0.05$ (versus non-stressed control) ##; $p<0.01$, #; $p<0.05$ (versus stress-loaded group), +; $p<0.05$ (versus anti-IL-6 antibody administration group), n=9).

Example 16

Effects of Anti-IL-18 Receptor Antibodies on Stress-Dependent Elevation of BUN in Disease Model Mice

Figure 17:
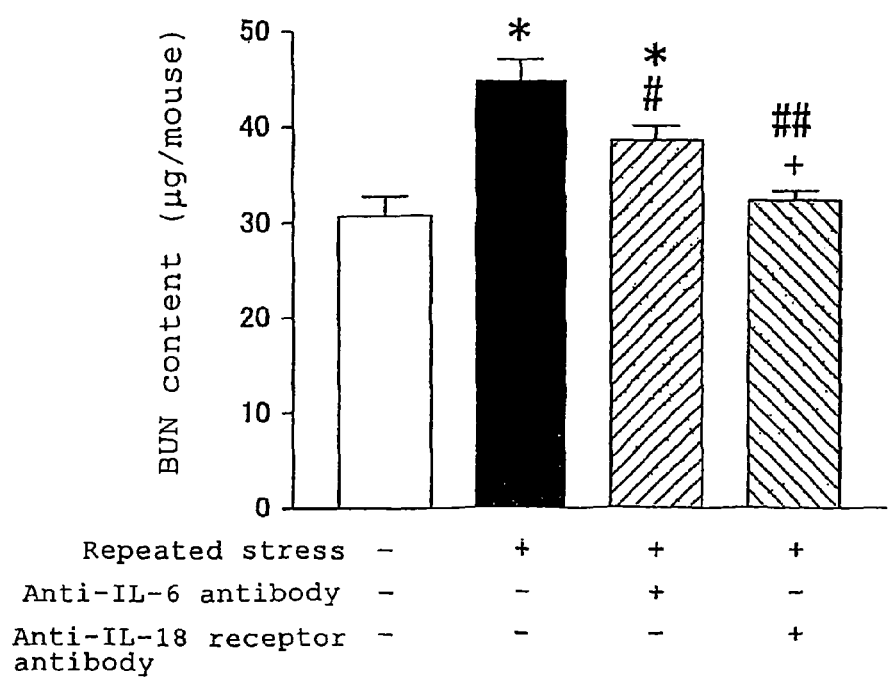
FIG. 17 is a drawing showing the effects of an anti-IL-6 antibody or an anti-IL-18 receptor antibody on the stress-dependent elevation of BUN in a mouse model of systemic lupus erythematosus.

BUN (blood urea nitrogen) in MRL/lpr mice (12 weeks) was measured in the same manner as Example 15 (FIG. 17).

In the MRL/lpr mice, BUN rose in the stress-loaded group, but the elevation of BUN was suppressed in the antibody administration group. The BUN in the group receiving anti-IL-18 receptor antibodies (anti-α antibody+anti-β antibody) at 25 µg/kg by intraperitoneal administration 10 minutes before stress loading was lower than that of the anti-IL-6 antibody administration group, and this was similar to the level in the non-stress-loaded group. (\*\*; p<0.01, \*; p<0.05 (versus non-stressed control), ##; p<0.01, #; p<0.05 (versus stress-loaded group), +; p<0.05 (versus anti-IL-6 antibody administration group), n=9).

The present invention is not limited to the above-described modes of embodiment, and permits various changes within the scope shown in the claims. Hence, modes of embodiment obtained by combining technical means altered as appropriate within the scope shown in the claims are also included in the technical scope of the present invention.

INDUSTRIAL APPLICABILITY

A pharmaceutical composition according to the present invention can be used as a keratinization-ameliorating agent that normalizes the abnormal keratinization of skin epidermal cells. Also, a pharmaceutical composition according to the present invention is capable of restoring the normal function of the skin by a remarkable suppressive action on epidermal thickening due to ultraviolet. Furthermore, a pharmaceutical composition according to the present invention is capable of suppressing epidermal thickening and preventing and/or treating skin cancer by suppressing the abnormal growth of keratinocytes and promoting the differentiation thereof.

The invention claimed is:

1. A method of inhibiting ultraviolet-dependent epidermal hardening or thickening in skin comprising applying a pharmaceutical comprising an antibody that specifically binds to a polypeptide consisting of the amino acid sequence set forth in SEQ ID NO: 9 to the skin after exposure to ultraviolet irradiation, wherein ultraviolet-dependent epidermal hardening or thickening is inhibited.

* * * * *